United States Patent [19]

Ohtsuka et al.

[11] 4,051,314

[45] Sept. 27, 1977

[54] POLYSACCHARIDES AND METHOD FOR PRODUCING SAME

[75] Inventors: Shigeto Ohtsuka; Saburo Ueno; Chikao Yoshikumi; Fumio Hirose, all of Tokyo; Yoshio Ohmura, Tanashi; Toshihiko Wada, Mibu; Takayoshi Fujii, Tokyo; Eiichi Takahashi, Urawa, all of Japan

[73] Assignee: Kureha Kagaku Kogyo Kabushiki Kaisha, Tokyo, Japan

[21] Appl. No.: 513,958

[22] Filed: Oct. 11, 1974

Related U.S. Application Data

[63] Continuation-in-part of Ser. No. 80,755, Oct. 14, 1970, abandoned.

[51] Int. Cl.² ............................................. C08B 37/00
[52] U.S. Cl. ..................................... 536/1; 195/31 P; 424/181
[58] Field of Search ..................... 260/209 R; 536/1

[56] References Cited

U.S. PATENT DOCUMENTS

| 3,301,848 | 1/1967 | Halleck | 260/209 R |
| 3,759,896 | 9/1973 | Komatsu et al. | 260/209 R |

OTHER PUBLICATIONS

Jimenez–Martinez, "Chem. Abst." vol. 72, 1970, p. 75847(b).

*Primary Examiner*—Johnnie R. Brown
*Attorney, Agent, or Firm*—Lane, Aitken, Dunner & Ziems

[57] ABSTRACT

Polysaccharides are produced by purifying a liquid extract of a mycelium of a strain of fungus species belonging to the class Basidiomycetes or the filtered broth of a cultured medium in which a mycelium of a selected strain of Basidiomycetes has been incubated; the polysaccharides exhibiting an anticarcinogenic activity in mice.

9 Claims, 29 Drawing Figures

FIG. 2.    FOMES FOMENTARIUS (FR.) KICKX

DAEDALEOPSIS TRICOLOR (F.R.) BOND. ET SING.

CYCLOMYCES FUSCUS KUNZE

PHELLINUS IGNIARIUS (FR.) QUÉL.

PHELLINUS ROBUSTUS (KARST.) BOURD. ET GALZ.

FIG. 27. CORIOLUS BIFORMIS (Klotz.) PAT.

POLYSACCHARIDES AND METHOD FOR PRODUCING SAME

CROSS-REFERENCE TO RELATED APPLICATION

This is a continuation-in-part of Ser. No. 80,755, filed Oct. 14, 1970 now abandoned.

BACKGROUND OF THE INVENTION

This invention relates to polysaccharides and to a process for their production from an extract or a cultered broth of a mycelium comprising a fungus species of the class Basidiomycetes. Such polysaccharides have been found to be effective in the treatment of cancerous tumors in mice.

While the extraction of unspecified substances having anti-cancerous activity from certain species of Basidiomycetes is known (Japanese Patent Publication Nos. 18196/1962, 16048/1968, and 25563/1968, for example, are generally directed to such a concept) these processes are not commercially feasible since they necessary use basidiocarps as the starting materials and the use of such materials is impractical for mass-production. In addition, the physicochemical properties of the products resulting from these processes were not known.

SUMMARY OF THE INVENTION

In accordance with the present invention polysaccharides are produced from a liquid extract of a mycelium of a fungus species belonging to the class Basidiomycetes or from a filtered broth of a culture in which such a mycelium has been incubated. The production of such polysaccharides is generally accomplished by treating the liquid extract or filtered broth so as to initially extract impurities, principally free proteins, therefrom and then subjecting the treated liquid to a series of additional procedures which remove therefrom residual impurities, such as acids, salts and organic compounds including ionic and low molecular weight components.

The free protein removal is optionally accomplished by acid treatment of the liquid extract or broth so as to precipitate the free proteins which are then separated therefrom by filtration. Alternatively, free proteins are removed in an ion-exchange column.

The residual impurities are removed from the treated liquid, and the polysaccharides recovered, by a procedure including one or more techniques selected from dialysis, gel infiltration, ion exchange, salting out, and ultrafiltration.

The products resulting from this purification process have been identified as polysaccharides, each of which has a molecule weight in figure of $10^5$. The precise structure of these substances has not been determined but each has an identifying infra-red spectrum set forth in FIGS. 1 - 21, respectively, and a carbon, hydrogen, nitrogen and oxygen content (%) specified hereinafter. But the oxygen content represents the balance, that is [100-(carbon content + hydrogen content + nitrogen content)]%.

Polysaccharides so produced have been found to exhibit anticarcinogenic activity in mice.

Accordingly, it is the primary object of this invention to recover polysaccharides from a liquid extract of a cultured mycelium of a fungus species of the class Basidiomycetes or the filtered cultured broth of such species.

It is another object of this invention to provide a commercially feasible process for recovering polysaccharides having anticarcinogenic activity from a liquid extract of a cultured mycelium of a fungus species of the class Basidiomycetes or a cultured broth of a mycelium of such species.

The accomplishment of these and other objects of the present invention will become apparent in the ensuing specification and claims.

DETAILED DESCRIPTION OF THE PREFERRED EMBODIMENTS

Figure 1:
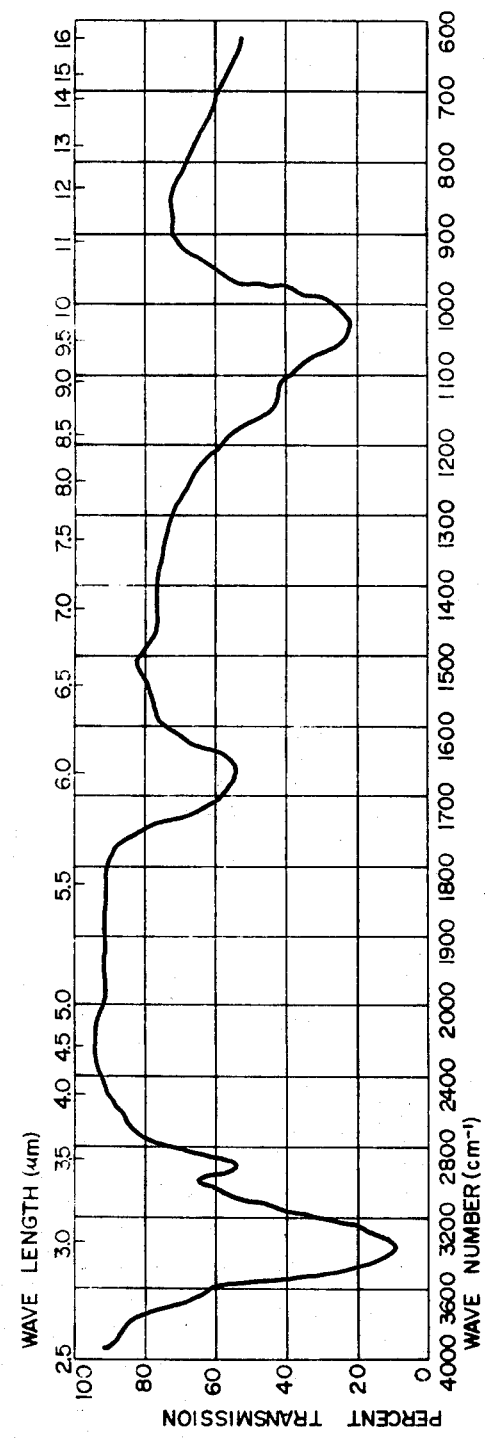
FIGS. 1 through 21 are infrared spectra of the polysaccharides produced according to this invention.
Figure 2:
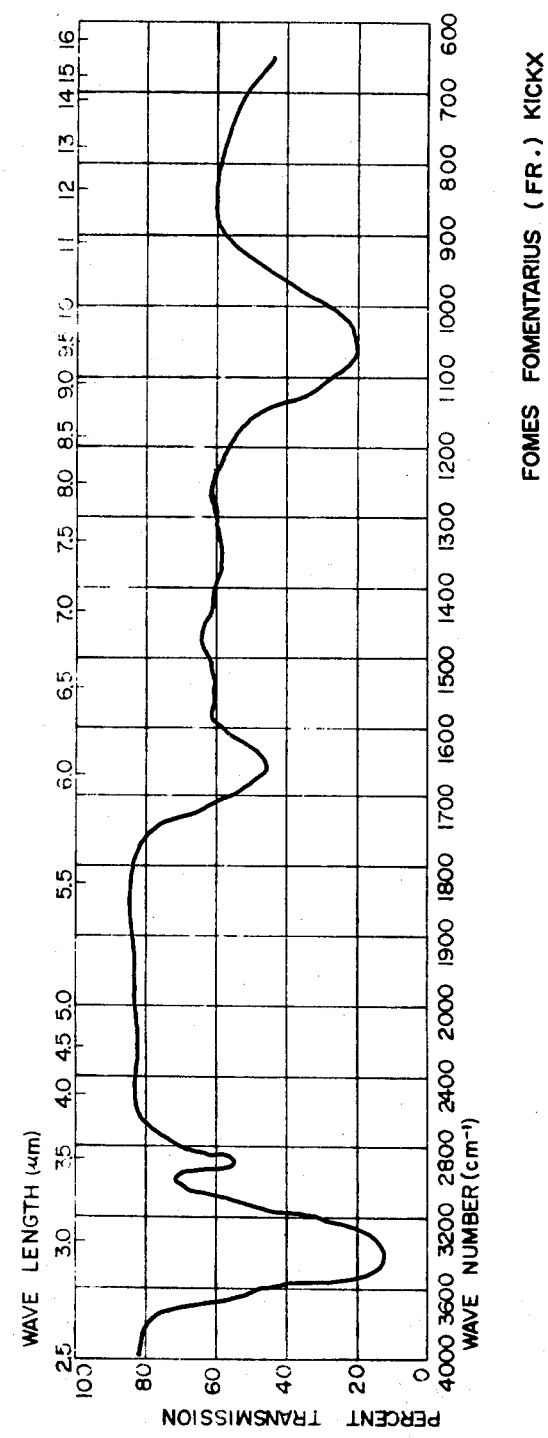
Figure 3:
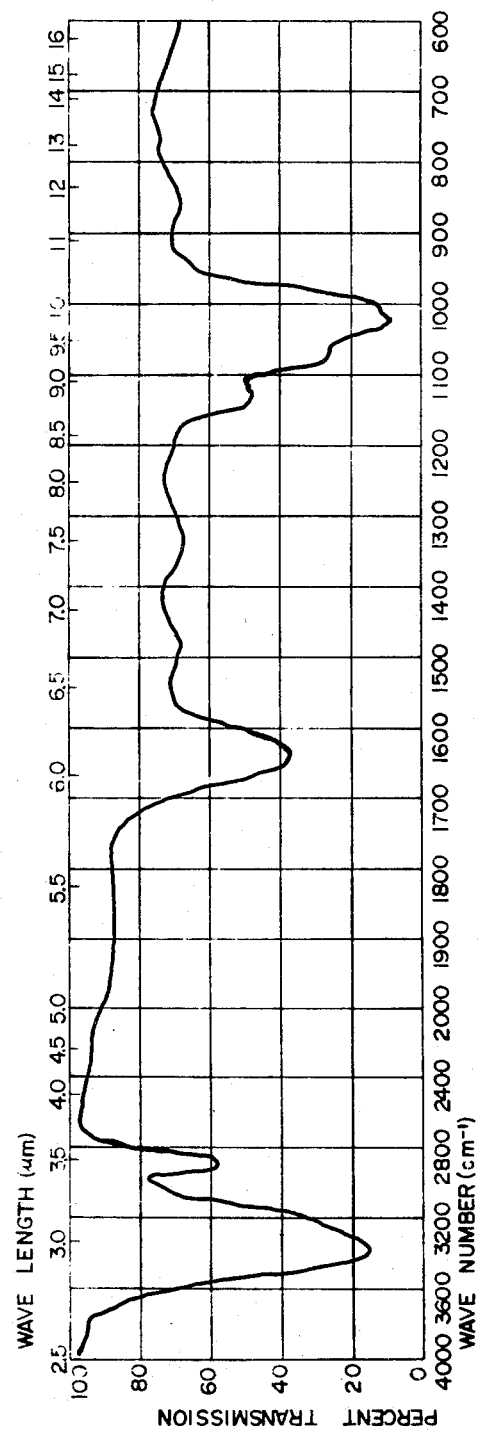
Figure 4:
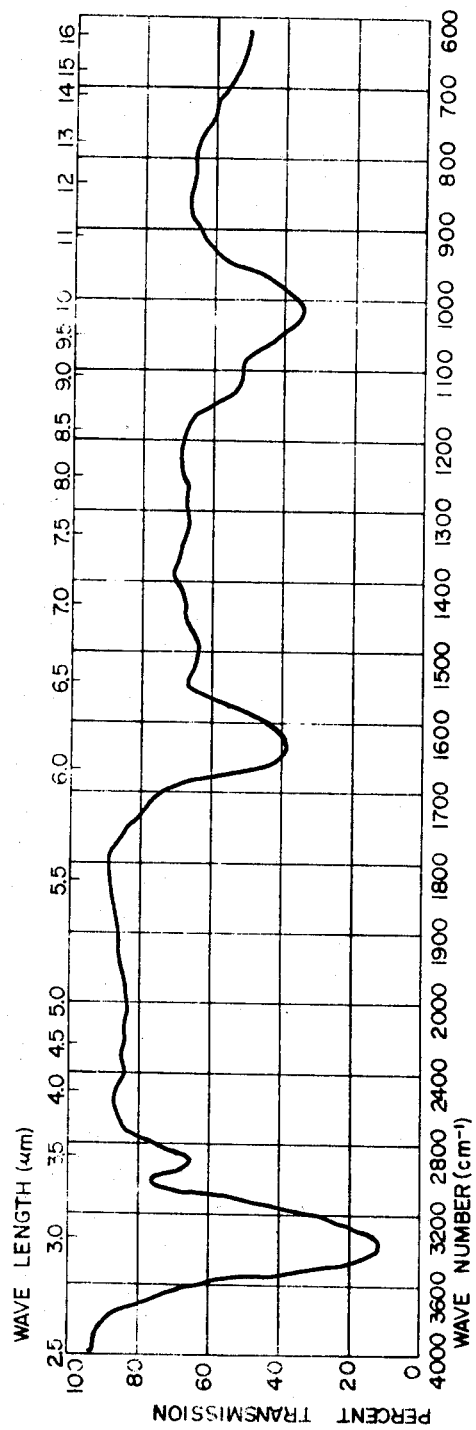
Figure 5:
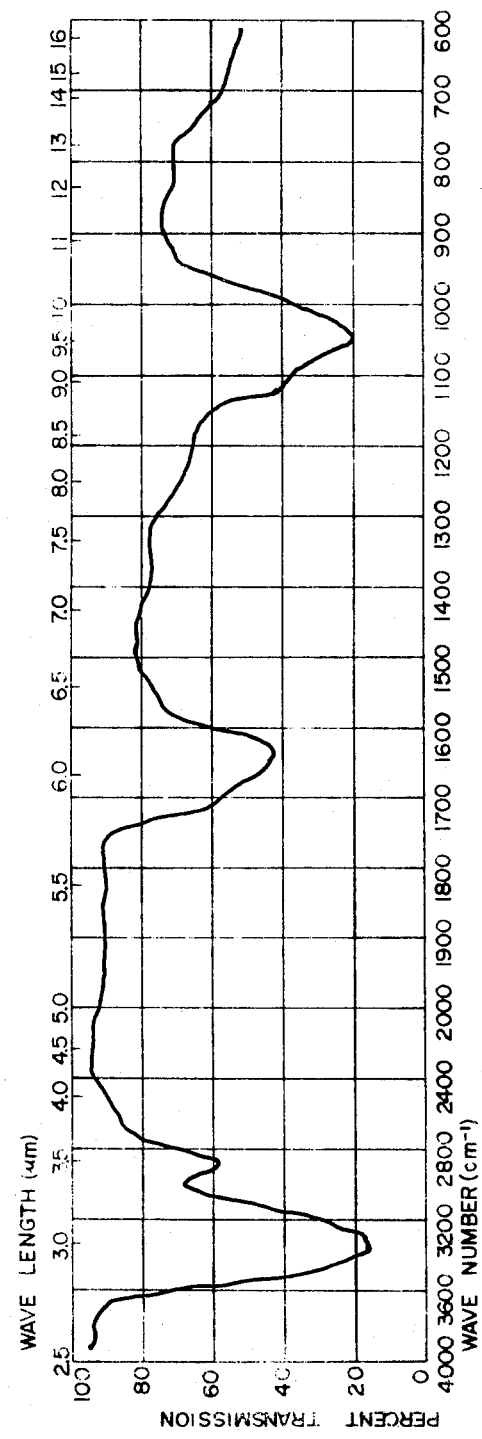
Figure 6:
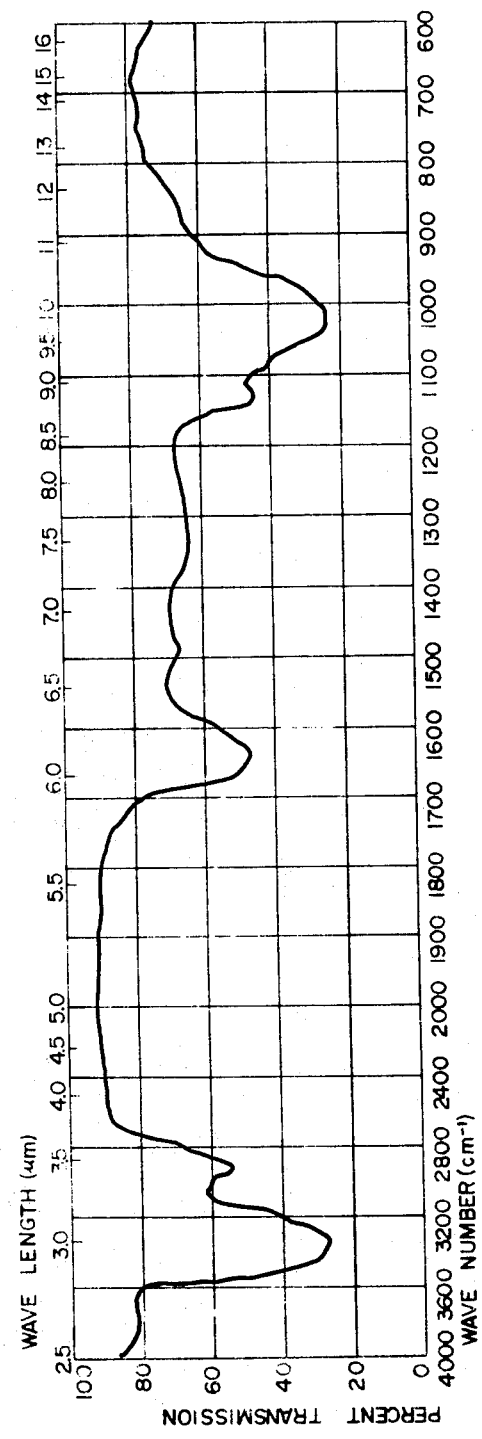
Figure 7:
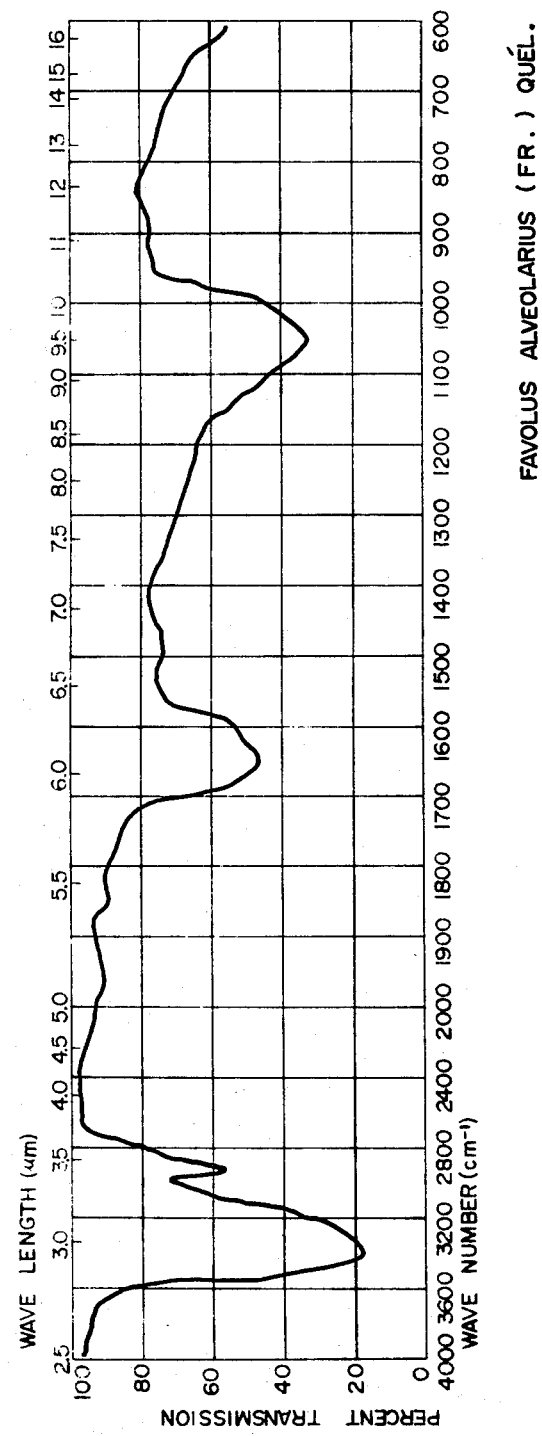
Figure 8:
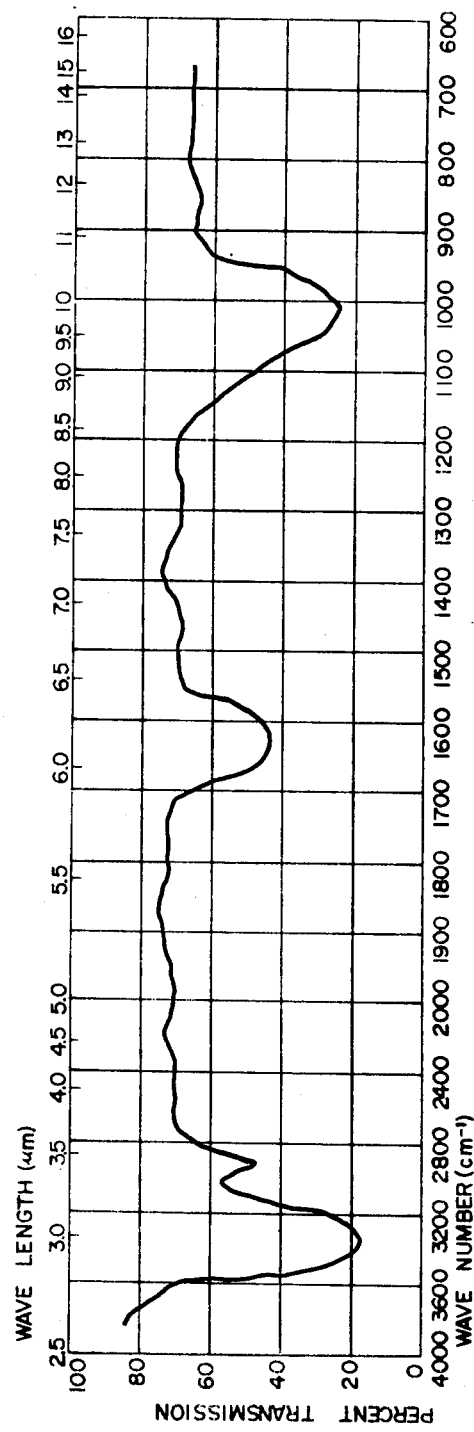
Figure 9:
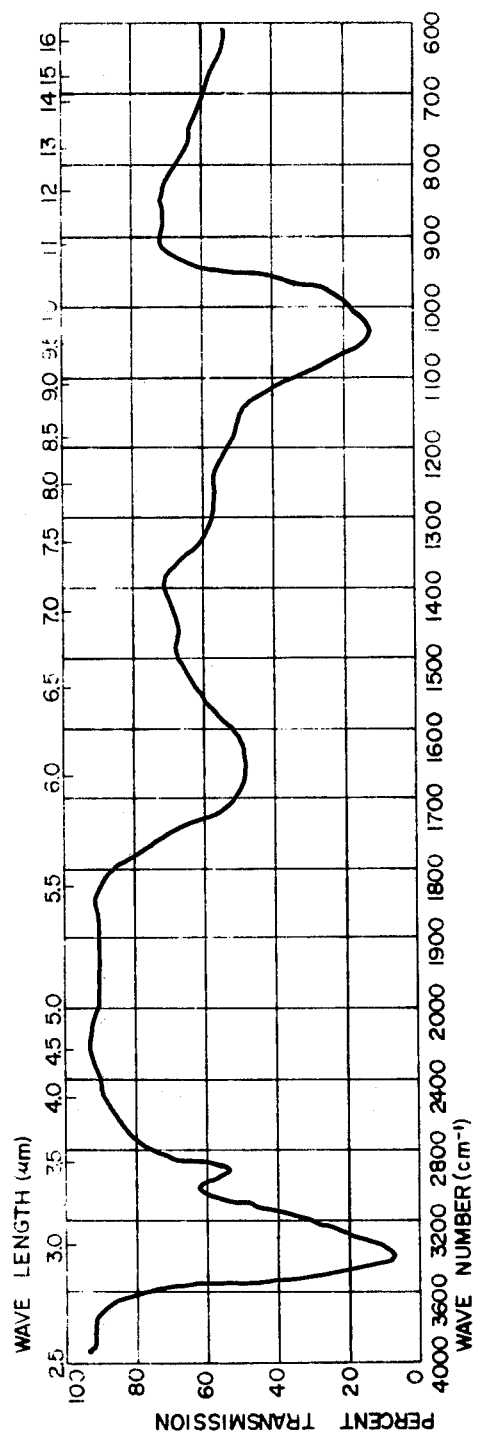
Figure 10:
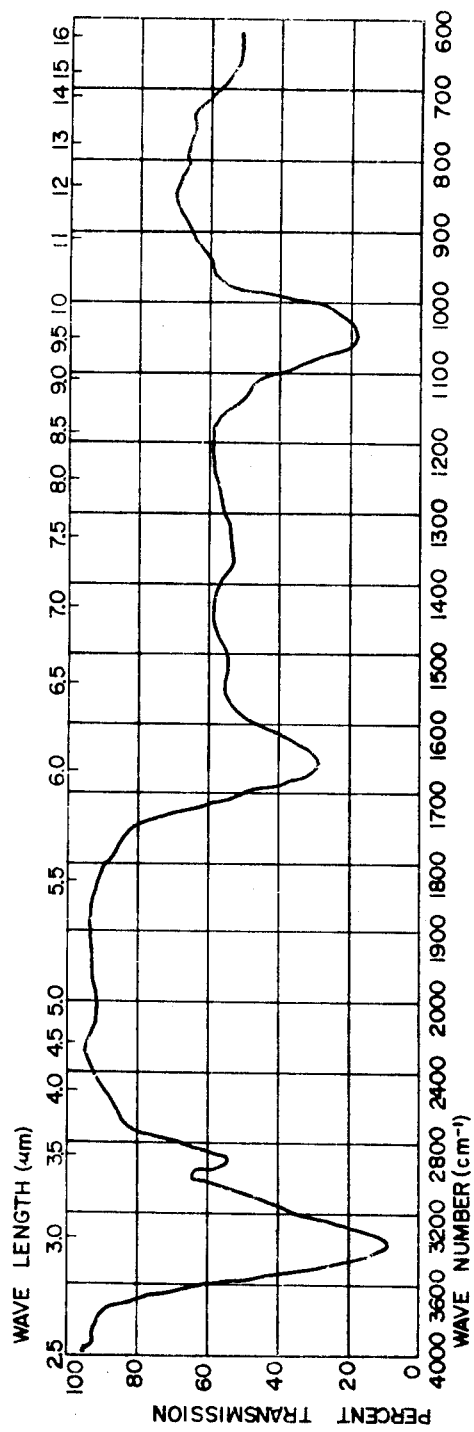
Figure 11:
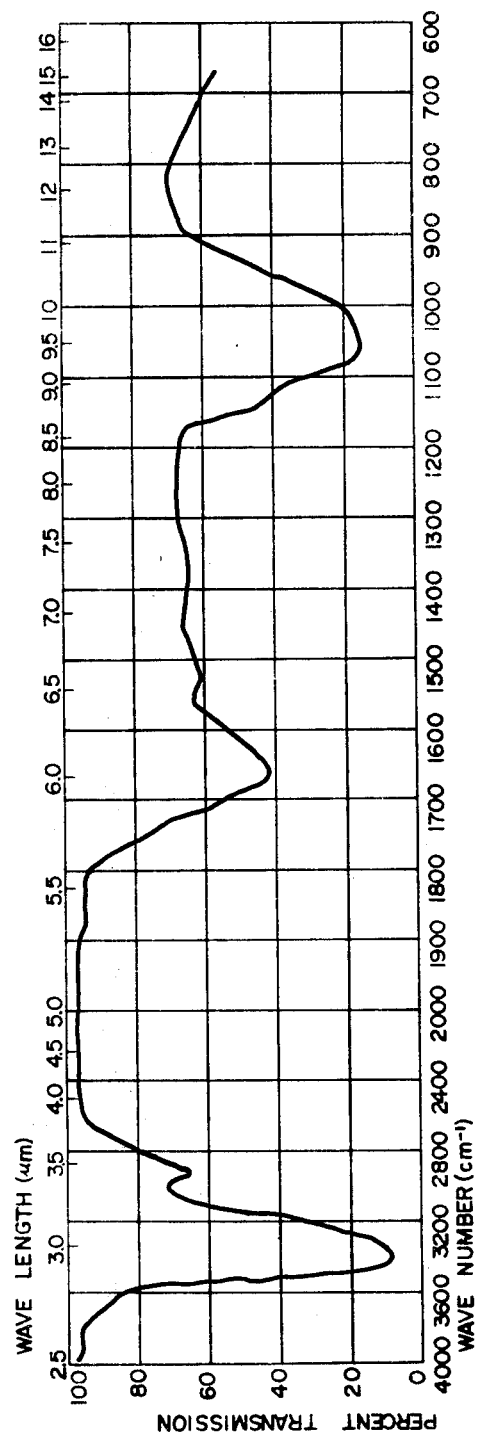
Figure 12:
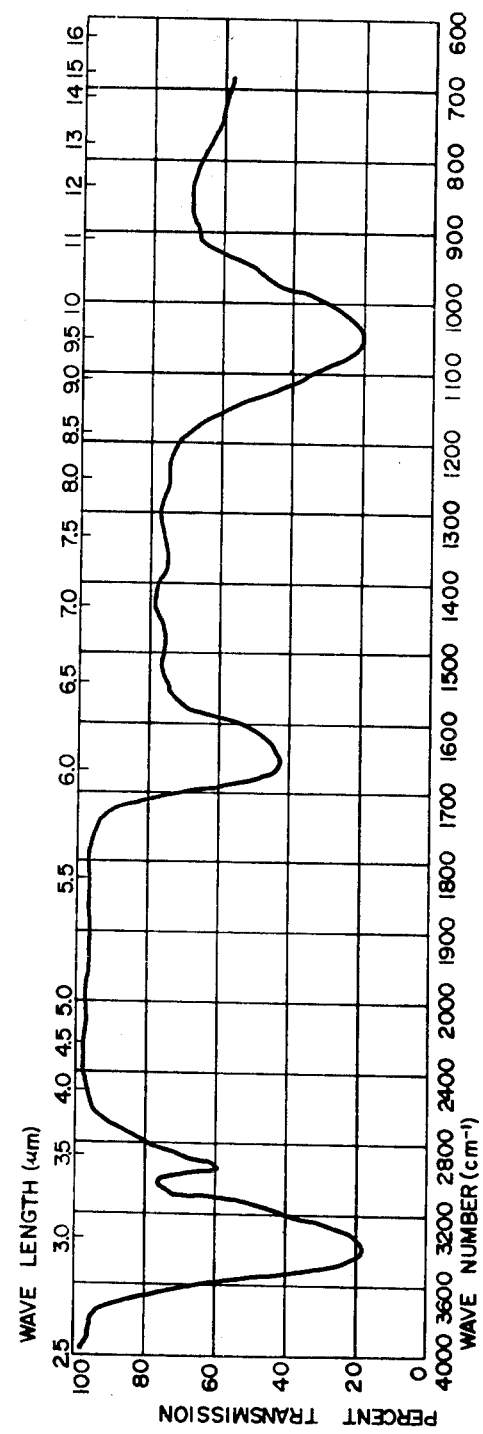
Figure 13:
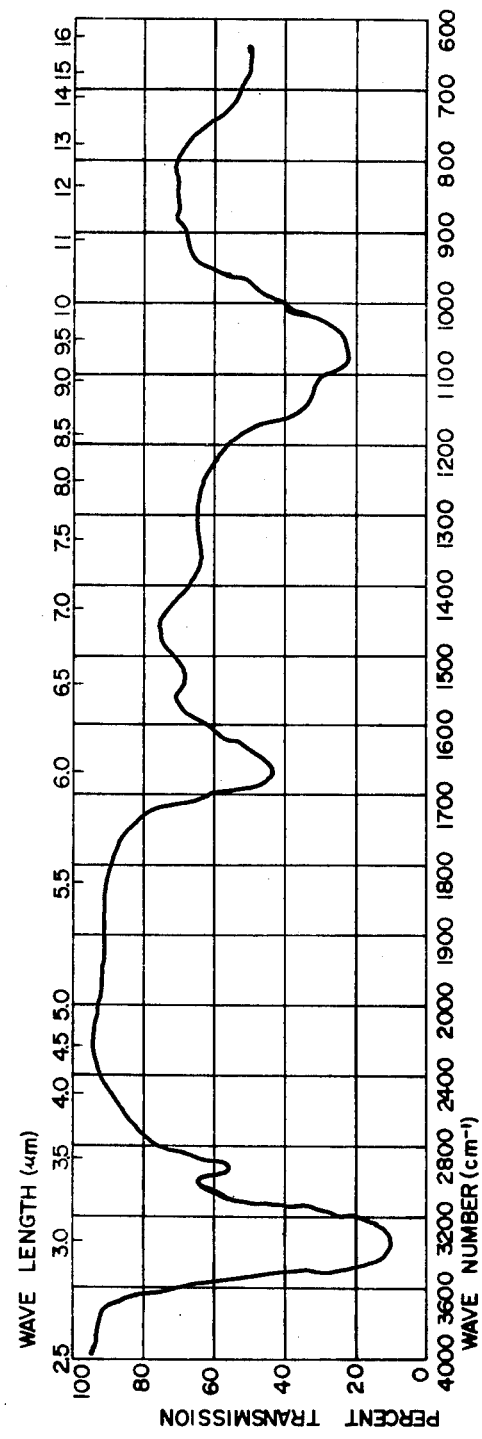
Figure 14:
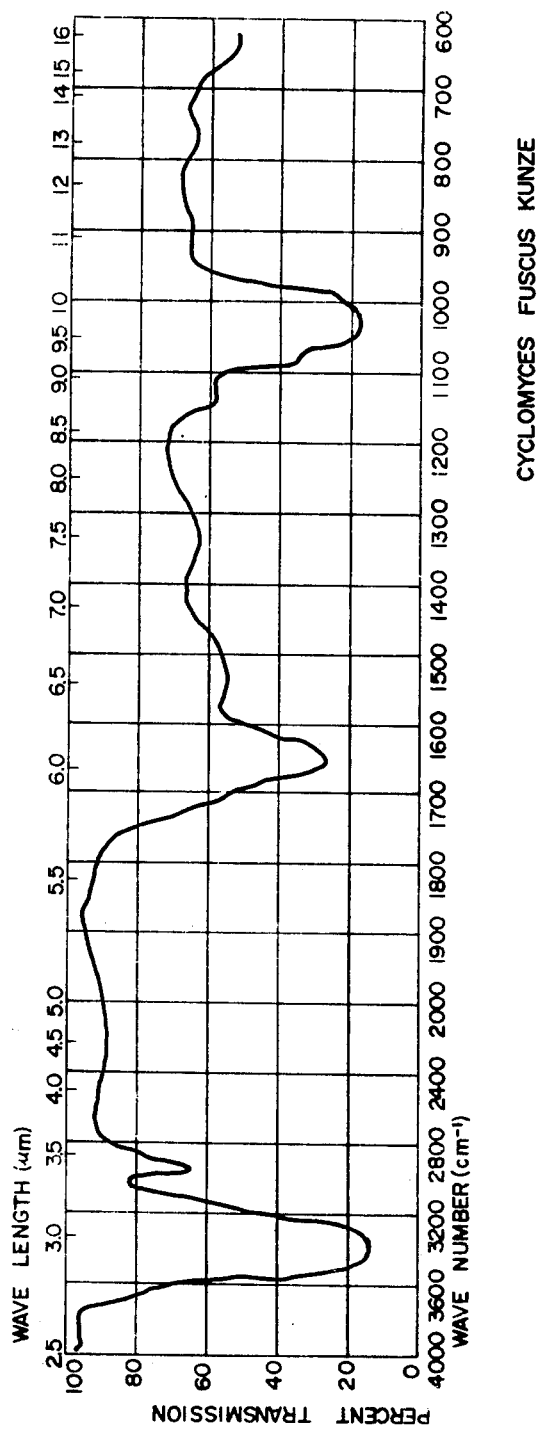
Figure 15:
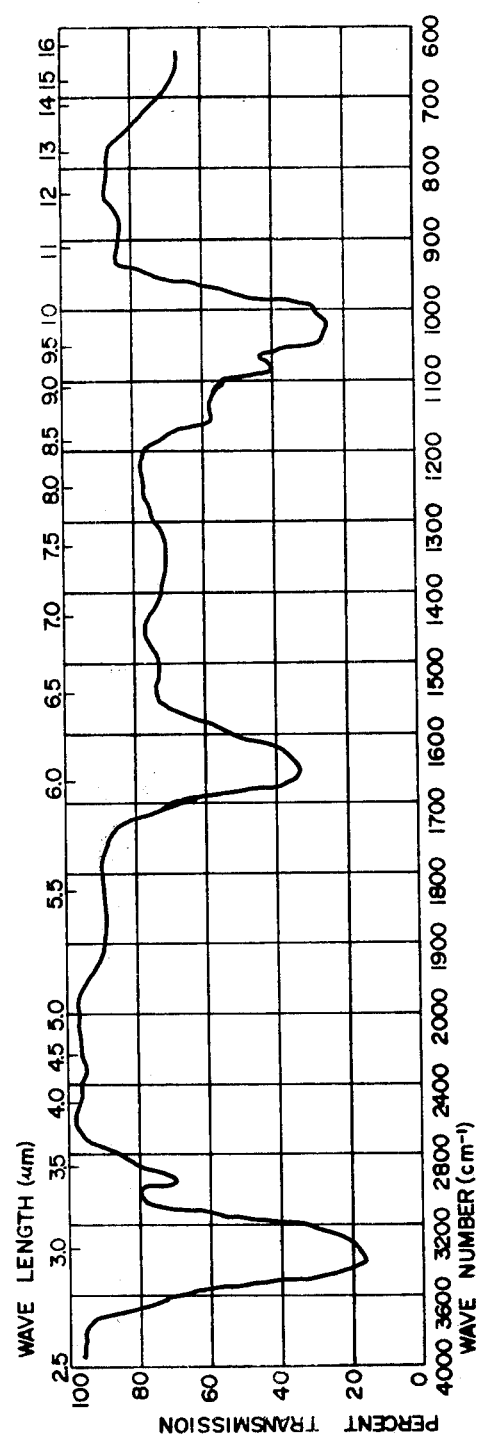
Figure 16:
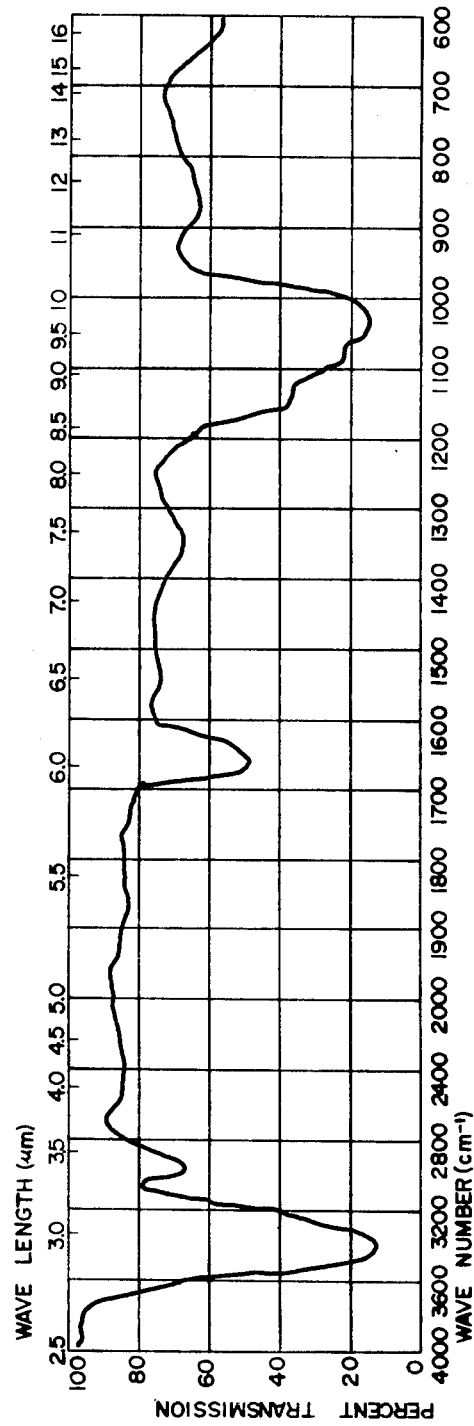
Figure 17:
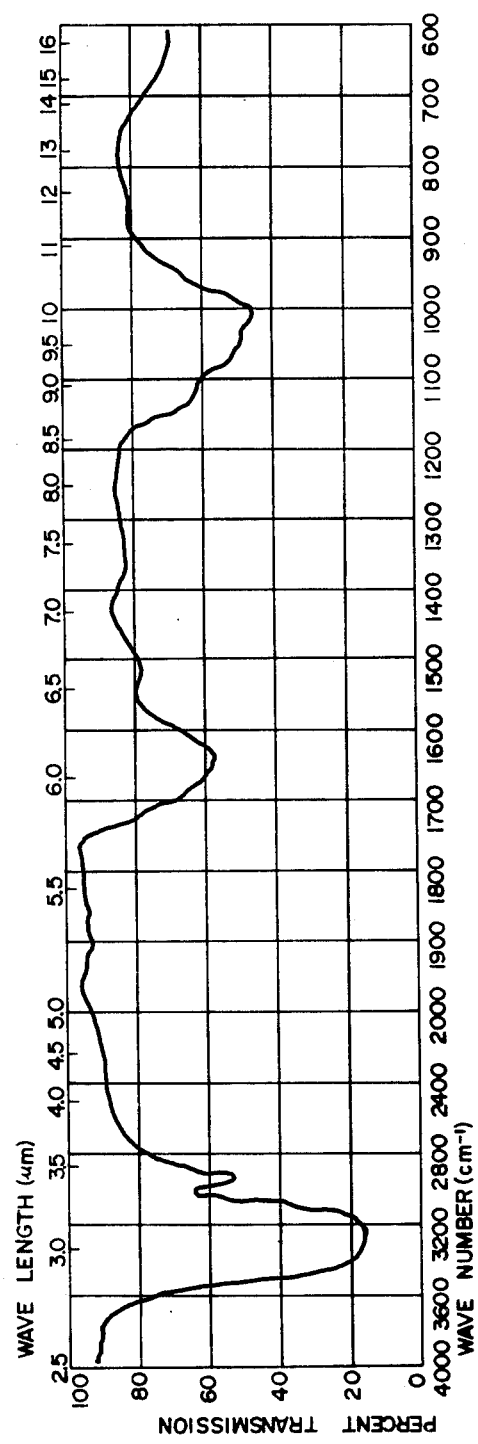
Figure 18:
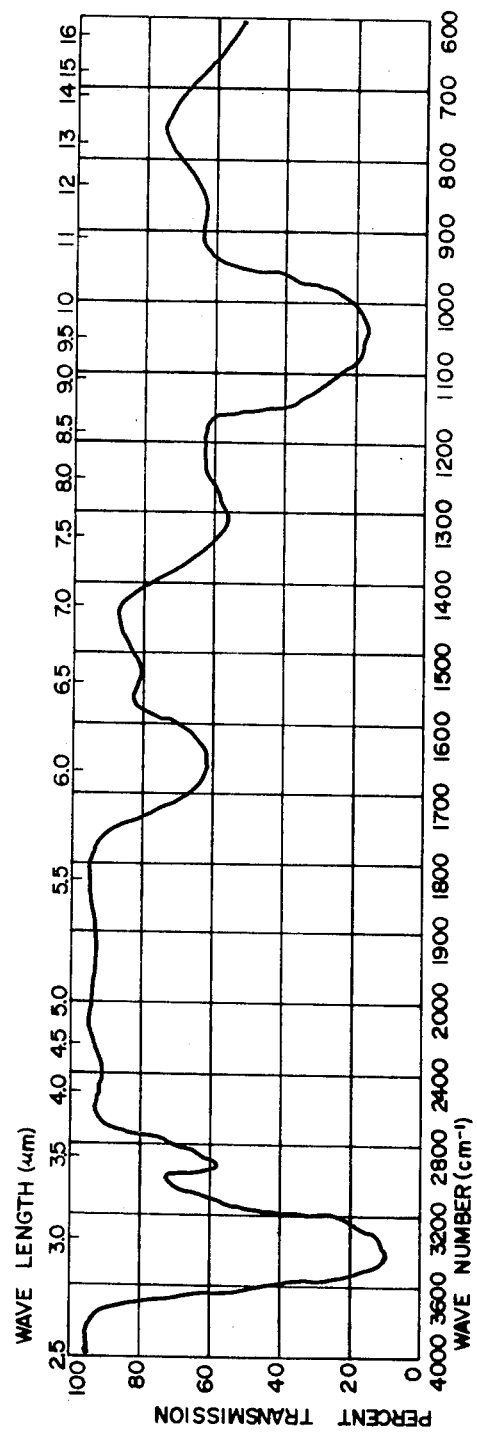
Figure 19:
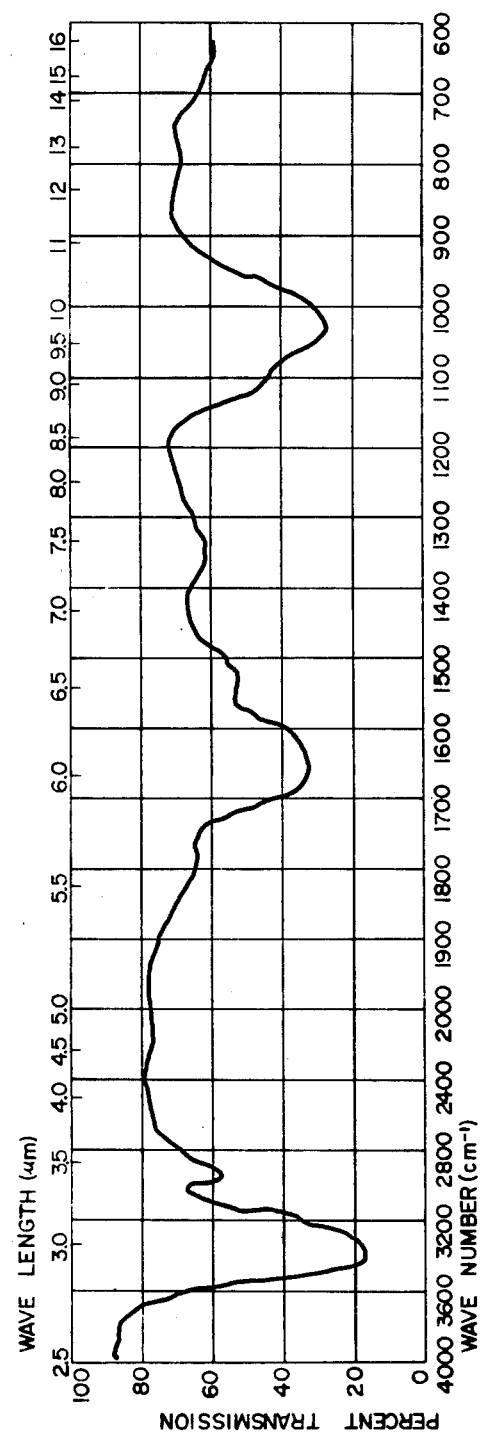
Figure 20:
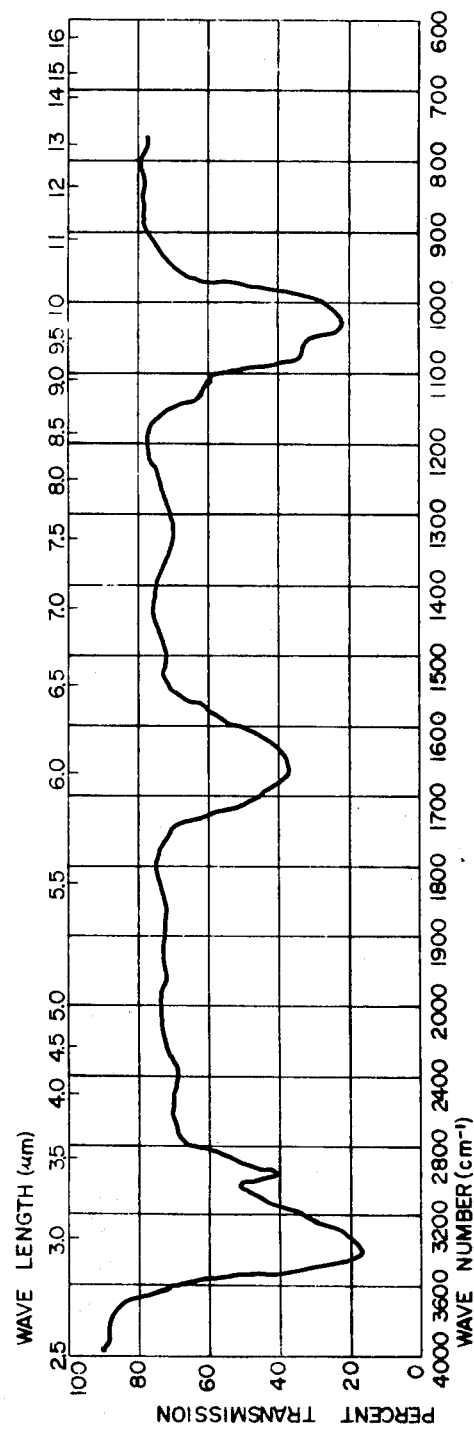
Figure 21:
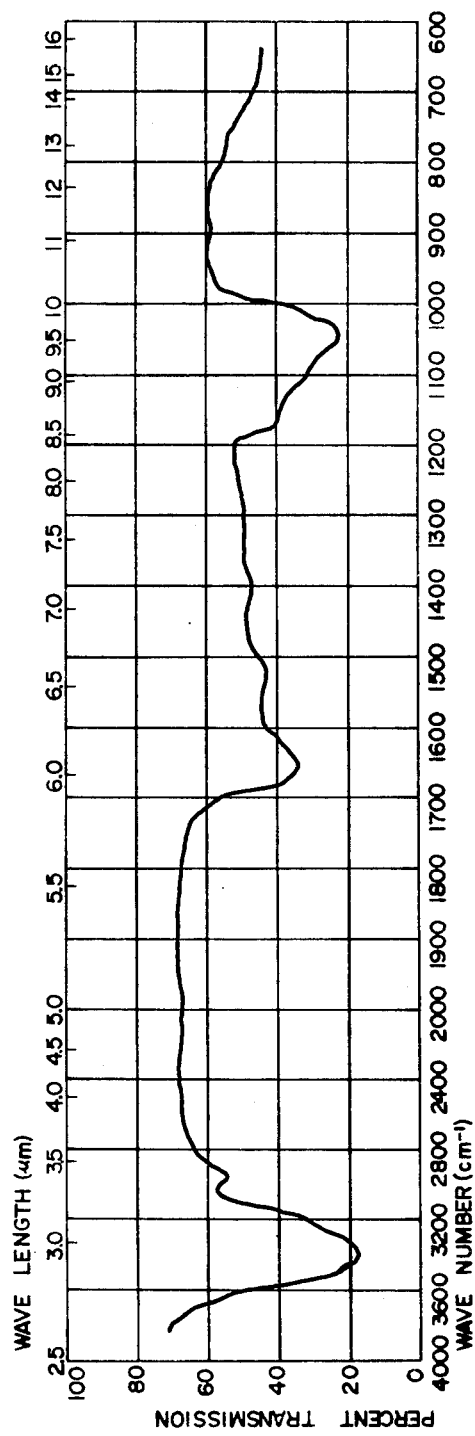

According to this invention, polysaccharides having anticarcinogenic activity are recovered from a liquid extract of a mycelium of a fungus species of the class Basidiomycetes or from the filtered cultured medium in which such species have been incubated. But the term "polysaccharide" used herein is meant not only a polysaccharide itself but also a polysaccharide-protein complex (mucopolysaccharide).

When a liquid extract is utilized in this process, the mycelium used as the starting material may be of natural origin or artificially propagated and it may be either in the raw state or in the conserved state, i.e., washed with water and dried by conventional methods or freeze-drying.

A liquid extract of this substance is produced by mixing the mycelium with hot water or a hot aqueous solution for a period of time to be determined by the temperature of the liquid. Although this temperature is not critical if maintained below 120° C, it will preferably be between 60° - 100° C.

Hot water is usually employed in an extracting operation but, as previously indicated, an aqueous solution of an organic solvent which is soluble in water, acid, base, salt and the like may also be employed. Within the above-indicated preferred temperature range, the extraction treatment is preferably carried out for a period of from 30 minutes to 10 hours. The extraction is desirably carried out under agitation in a vessel which may be made of glass, glass-lined, enameled or stainless steel and the use of a mycelium which has been previously pulverized is particularly effective. In any event, after the extraction treatment is completed, the extracted mycelium and other solid matters are removed from the liquid extract by any convenient means, such as filtration or centrifugal separation, and the liquid extract is concentrated for further treatment.

The extract obtained as described above is then purified according to the procedure described below, resulting in the precipitation and recovery of the intended polysaccharides. When the term "liquid extract" is used hereinafter it is intended to means the filtrate or centrifugate from which the aforementioned solid matters have been removed.

When the filtered cultured broth of a species belonging to Basidiomycetes is used as the starting material, the broth may be utilized by the ordinary culture condition of the species. The broth is filtered to remove the incubated mycelium but the effective compounds, i.e., polysaccharides, remain in the filtrate. Thus, as used herein the term "filtered broth" is defined as the liquid medium containing the extracted polysaccharide which remains after the incubated mycelium has been removed. The term "cultured broth" is defined as the culture meium in which a species of Basidiomycetes has been incubated and the incubated mycelium and the liquid medium have been contained. After the broth is freed from the mycelium, it is concentrated and subjected to the purification treatment described below.

It is possible, of course, to mix a liquid extract and a filtered cultured broth so that they may be collectively subjected to the following purification treatment since the extract or broth contains the anticarcinogenic polysaccharide, and unnecessary substances such as free proteins, nucleic acids, reducing sugars, and the like. In general, the process comrpises (a) treating the filtered cultured broth or liquid extract so as to remove free proteins and other solid matters therefrom; (b) removing acids, ions and low molecular weight organic materials by a procedure selected from dialysis, gel filtration, ion exchange treatment, ultrafiltration and combination thereof to produce a substantially purified solution from which the intended polysaccharide is isolated; if necessary, (c) precipitating said polysaccharide from said substantially purified liquid extract or filtered cultured broth by a procedure selected from adding a highly polar organic solvent thereto and salting out.

Deproteinization of a liquid extract or filtered cultured broth may be carried out by adding thereto an inorganic or organic acid such as sulfuric acid, hydrochloric acid, nitric acid, acetic acid, trichloroacetic acid, picric acid, sulfosalicylic acid, tannic acid, etc., in an amount which is 0.1 - 3% by weight of the total liquid to precipitate free proteins, which are separated from the liquid extract or filtered cultured broth and discarded. Usually the effluent will be treated by a procedure selected from ion-exchange treatment, dialysis, gel filtration, ultrafiltration and combination thereof to effect decoloration, deacidification and removal of low molecular weight materials.

Ion-exchange is carried out using an anion-/and cation-exchange resin. Utilizable as cation exchange resins are, for example, Amberlite IR-120B, Amberlite 200, Amberlite IR122, Amberlite IR-123, Amberlite XE-100, Amberlite IRC-50 and Amberlite IRC-84 (the foregoing are the products marketed by Rohm & Haas); Dowex 50W (the product of Dow Chemical); Duolite C-3, Duolite C-1, Duolite C-20, Duolite C-25, Duolite C-27, Duolite ES-63, Duolite ES-80, and Duolite CS-101 (the foregoing are the products of Diamond Alkali Corporation); and Diaion SK-1A, Diaion SK-1B, Diaion SK-102, Diaion SK-103, Diaion SK-104, Diaion SK-106, Diaion SK-110, Diaion SK-112, Diaion SK-116, Diaion SK-1, Diaion PK-204, Diaion PK-208, Diaion PK-212, Diaion PK-216, and Diaion PK-228 (the foregoing being the products of Mitsubishi Chemical Industry Co., Ltd.). Utilizable as anion exchange resins are, for example, Amberlite IRA-400, Amberlite IRA-401, Amberlite IRA-402, Amberlite IRA-405, Amberlite IRA-425, Amberlite IRA-900, Amberlite IRA-904, Amberlite IRA-410, Amberlite IRA-411, Amberlite IRA-911, Amberlite IRA-910, Amberlite IRA-45, Amberlite IRA-93, Amberlite IRA-68, and Amberlite IR-4B (the foregoing are the products marketed by Rohm & Haas); Dowex 1, Dowex 2, Dowex 44, Dowex 21K and Dowex 11 (the products of Dow Chemical Corporation), and Duolite A-2, Duolite A-4, Duolite A-6, Duolite A-7, Duolite ES-15, Duolite A-30T, Duolite A-30B, Duolite A-41, Duolite A-43, Duolite ES-57, Duolite A-40, Duolite A-40LC, Duolite A-42, Duolite A-42LC, Duolite A-101, Duolite A-101D, Duolite A-102, Duolite A-120D and Duolite ES-111 (the products of Diamond Alkali Corporation).

Above all, Duolite S-30 or Duolite ES-33 (the products of Diamond Alkali Corp.), and the like, exhibit a strong effect on decoloration. An especially effective method for removing nucleic acids is to pass the liquid to be treated through Dowex 50WX2 (H-type) and Dowex 44 (OH-type).

Dialysis is a means for removing lower sugars, free amino acids, various salts, various nucleic acids, etc., and can be carried out using a semi-permeable membrane such as cellophane membrane, collodion membrane, gut membrane, etc.

Gel filtration is a means for removing lower sugars, free amino acids, various salts, various nucleic acids, etc., and can be carried out using a column pucked with dextrane or polyacrylamide gel, for example Sephadex G-10, G-15, G-25, G-50, G-75 (the foregoing are the product marketed by Pharmacia Fine Chemicals A B Uppsala, Sweden), Biogel P-2, P-4, P-6, P-10, P-30, P-60, P-100, P-150, P-200, P-300 (the foregoing are the product marketed by Bio-Rad Laboratories, California, the United States of America).

Ultra filtration is a means for removing lower sugars, free amino acids, various salts, various nucleic acids, etc., and can be carried out using a ultrafiltration apparatus.

Ultra filtration is a process for removing said impurities from a solution by making the solution pass through the membrane under pressure.

For isolating the effective substance of this invention from the liquid extract or filtered cultured broth purified in a manner as described above, there are several methods of forming precipitates; for example, treatment with lead acetate, salting out, treatment with a highly polar organic solvent, freeze drying etc.

The term "salting out" as used herein means the addition of water-soluble inorganic salt such as ammonium sulfate, edible salt, potassium chloride, barium carbonate or the like into the liquid extract to form a precipitate, in this instance the end product. When barium hydroxide is added, the resulting precipitate should be washed with hydrobromic acid to remove residual barium hydroxide. The addition of a highly polar organic solvent, including water-soluble alcohols and ketones such as methanol, ethanol, propanol, butanol, acetone, etc., also serves to form such a precipitate.

When the highly polar organic solvent is used, for example an alcohol, the liquid in the dialysis membrane or the effluent from the ion exchange columns is concentrated and the alcohol is added to the concentrated liquid in an amount 3 - 10 times the volume of the liquid to form a precipitate.

A lead acetate treatment includes the addition of lead acetate into the liquid extract to precipitate the end product as its lead salt. The end product can be obtained from the lead-containing precipitate by introducing hydrogen sulfide into a slurry of the precipitate to remove lead as lead sulfide.

Regardless of which method is used, the resulting precipitate is subjected to freeze-drying or to washing with alcohol and then with acetone followed by drying to produce a product which is a non-hygroscopic, powdery substance believed to be a polysaccharide for reasons described below.

The substance obtained by the foregoing treatments possesses the following characteristics: grayish white powder, non-dialyzable, without sharp melting point, carbonized by strong heating, insoluble in common organic solvents and organic acids and soluble in water. A 10% aqueous solution of this substance is neutral while a 0.1% aqueous solution thereof shows no characteristics absorption in ultraviolet range.

When the product is subjected, in a 0.05 mol sodium borate solution, to electrophoresis using a cellulose acetate membrane at 20 – 25V. cm for 90 minutes, only one spot is detected at the anode side. This means the product shows a very purified material.

However, when the 0.1% aqueous solution of this substance is hydrolyzed by adding sulfuric acid to the solution to make the normality of the solution unity, heated for 5 hours at 100° C., then neutralized by adding barium carbonate to the solution, and subjected to paper chromatographic analysis, glucose is detected without fail.

The hydrolyzate of the effective substance of this invention is positive to all of the reaction such as the anisaldehyde reaction, Molisch reaction, the anthrone reaction, the tryptophane sulfuric acid reaction, the chromotropic acid-sulfuric acid reaction, the carbazole-cysteins-sulfuric acid reaction, the aniline-hydrochloric acid reaction, the resorcinolhydrochloric acid reaction, Tollens reaction and the thioglycolsulfuric acid reaction, ninhydrin reaction, but negative to the ferric chloride reaction and Fehling reaction.

Considering all of the foregoing characteristics, the effective substance obtained according to this invention is believed to be a "polysaccharide".

The molecular weight of the polysaccharides was determined to be in figure of $10^5$, i.e., within the range $(1.0 – 1.9) \times 10^5$, according to the gel filtration method. A complete description of this method may be found in Granath et al., J. Chromatog 28, 69 – 81 (1967). In general, according to this method, the molecular weight of a water-soluble polymer is estimated according to a partition coefficient (Kav) which is calculated according to the following formula:

$$Kav = Ve - Vo/Vt - Vo$$

wherein $Vt$ represents the total volume, $Vo$ the void volume of the gel bed used, and $Ve$ represents the elution volume of the sample.

In determining the molecular weights of the polysaccharides of this invention Sephadex G-200® (a product of Pharmacia Fine Chemicals) was used as the gel bed with distilled water being the effluent used and identification made by the phenol-sulfuric acid method (calculated as D-glucose).

The standard correlation curve was drawn by using γ-globulin of human being (M.W. 160000), dextran (M.W. 150000), egg albumin (M.W. 44000), α-chymotrypsinogen (M.W. 23000) and myoglobin (M.W. 16800) as the standard substances with known molecular weights.

Figure 22:
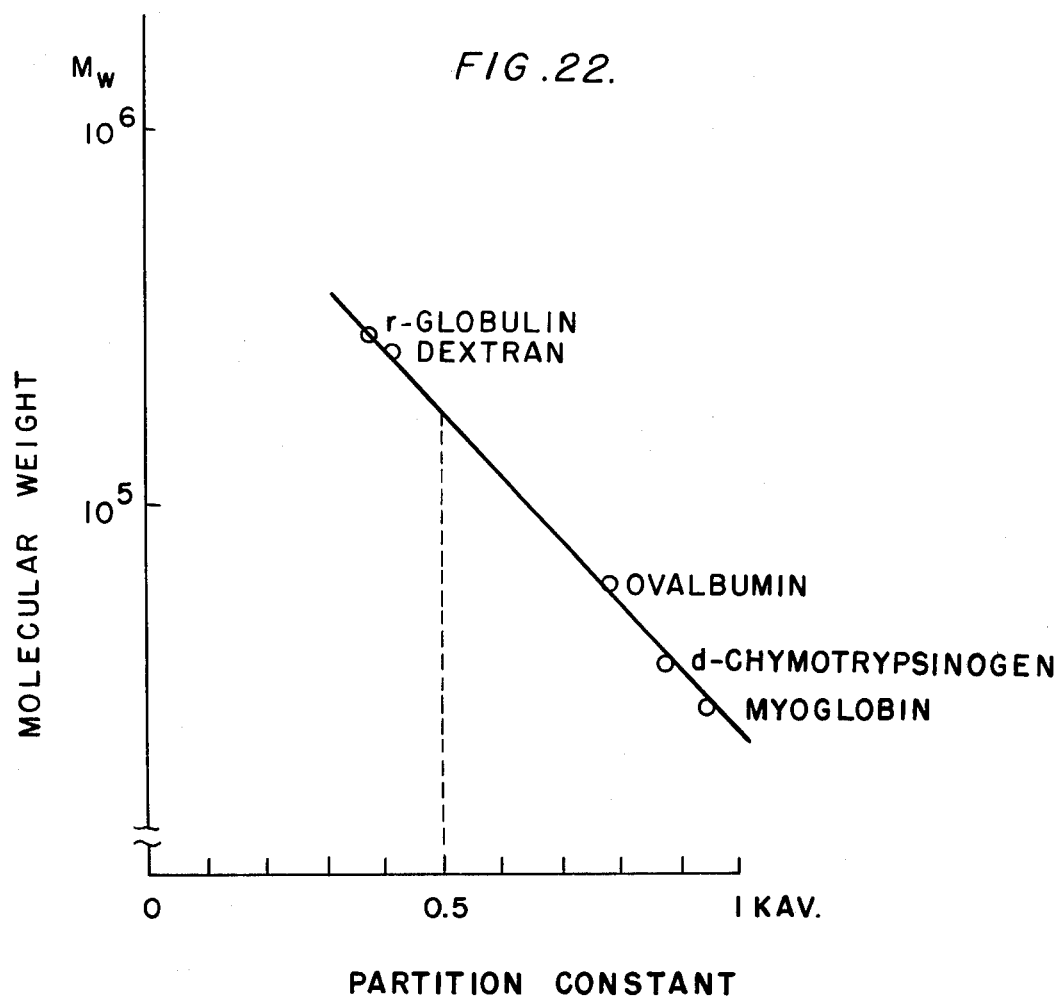
FIG. 22 is a drawing of the standard correlation curve used in this invention in determining the molecular weight of each polysaccharide.
Figure 23:
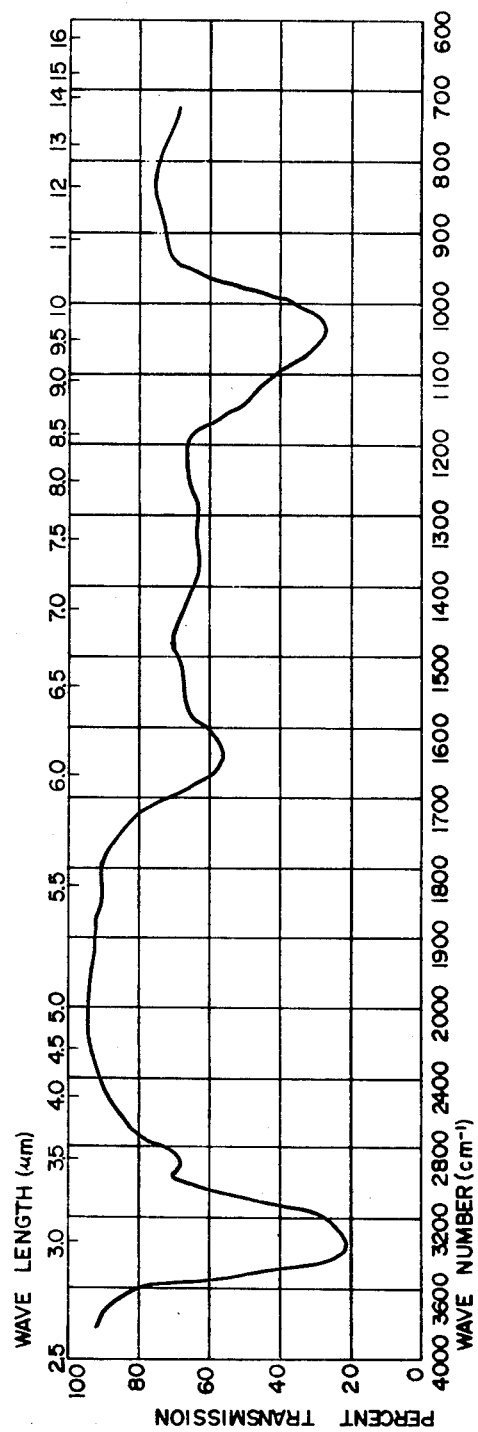
Figure 24:
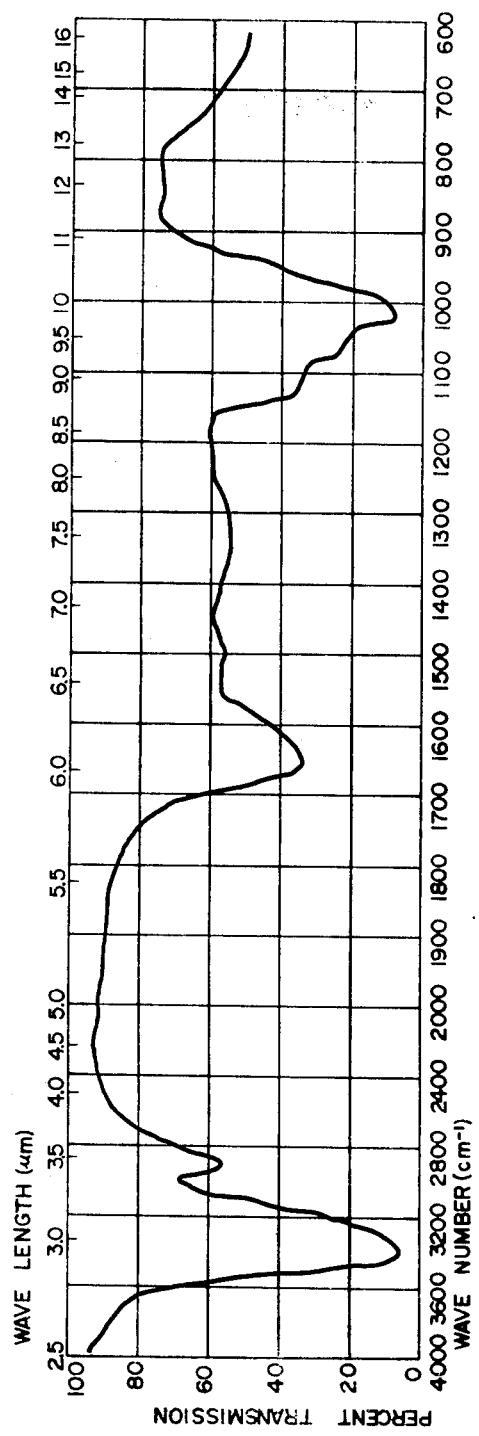
Figure 25:
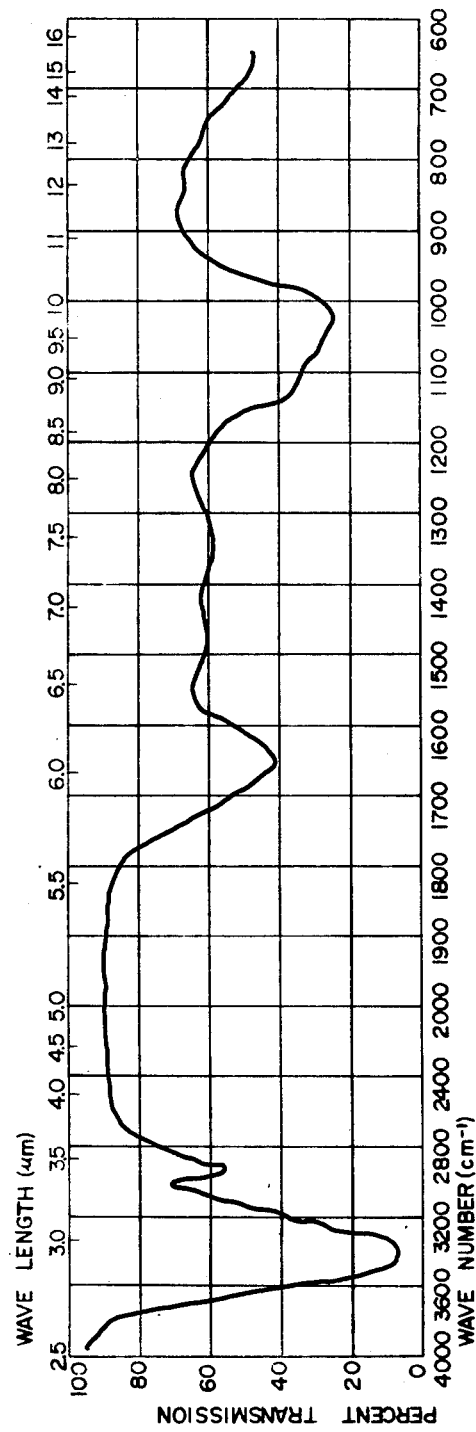
Figure 26:
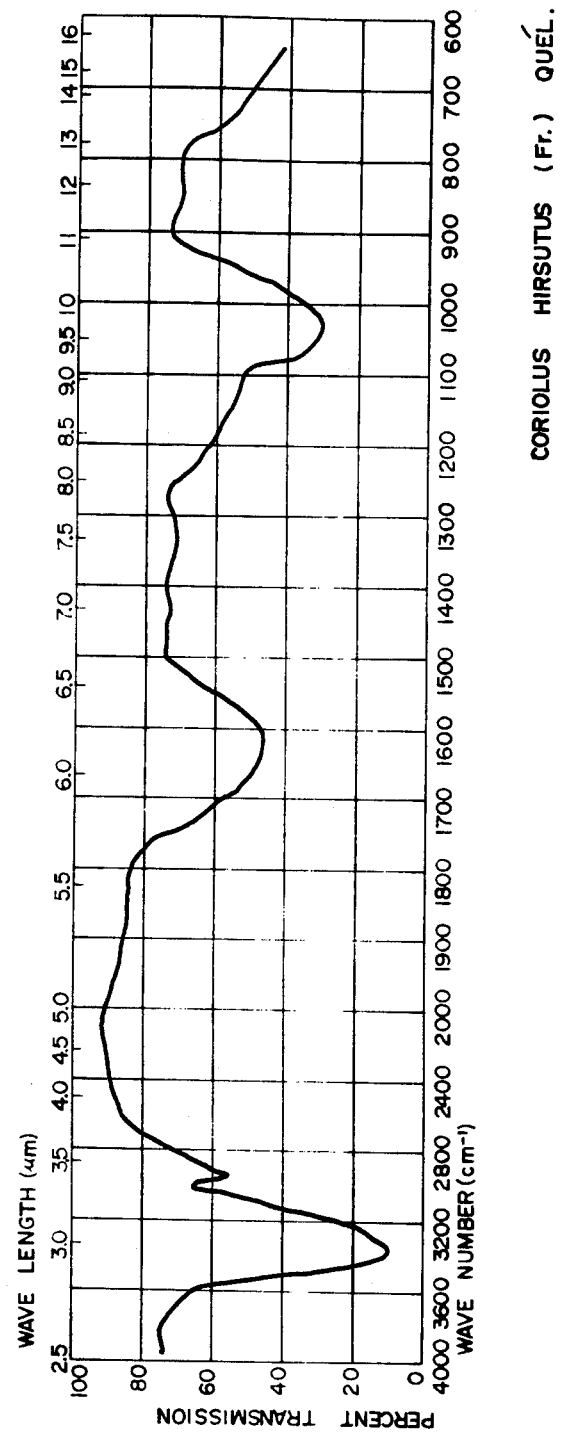
Figure 27:
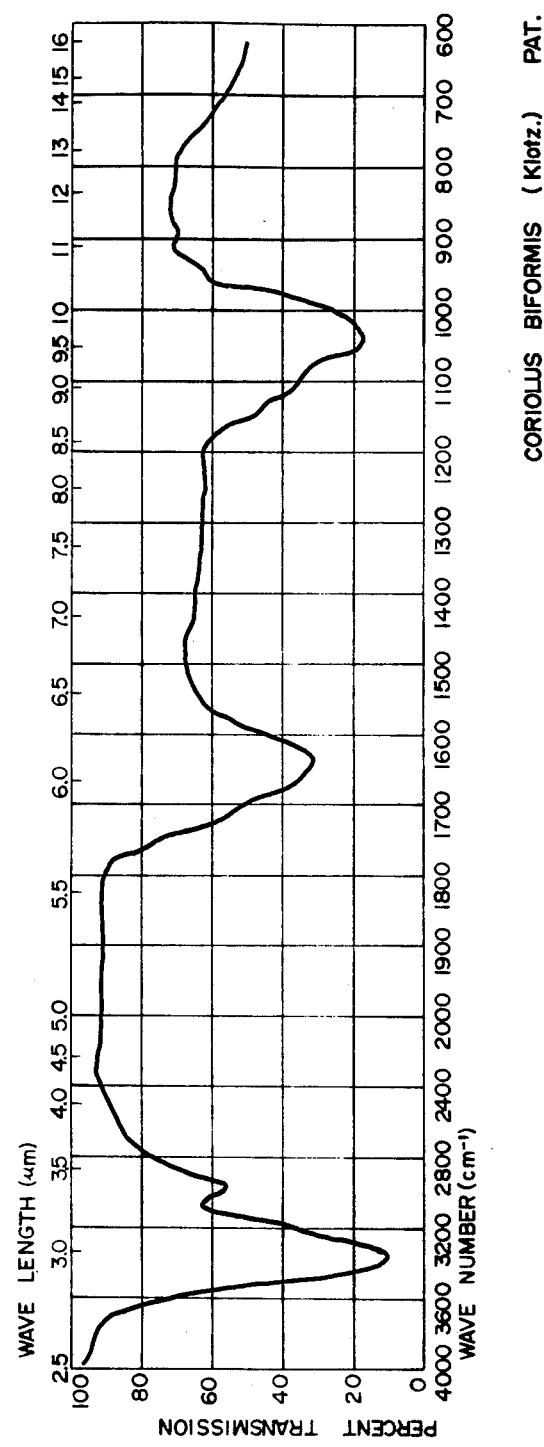
Figure 28:
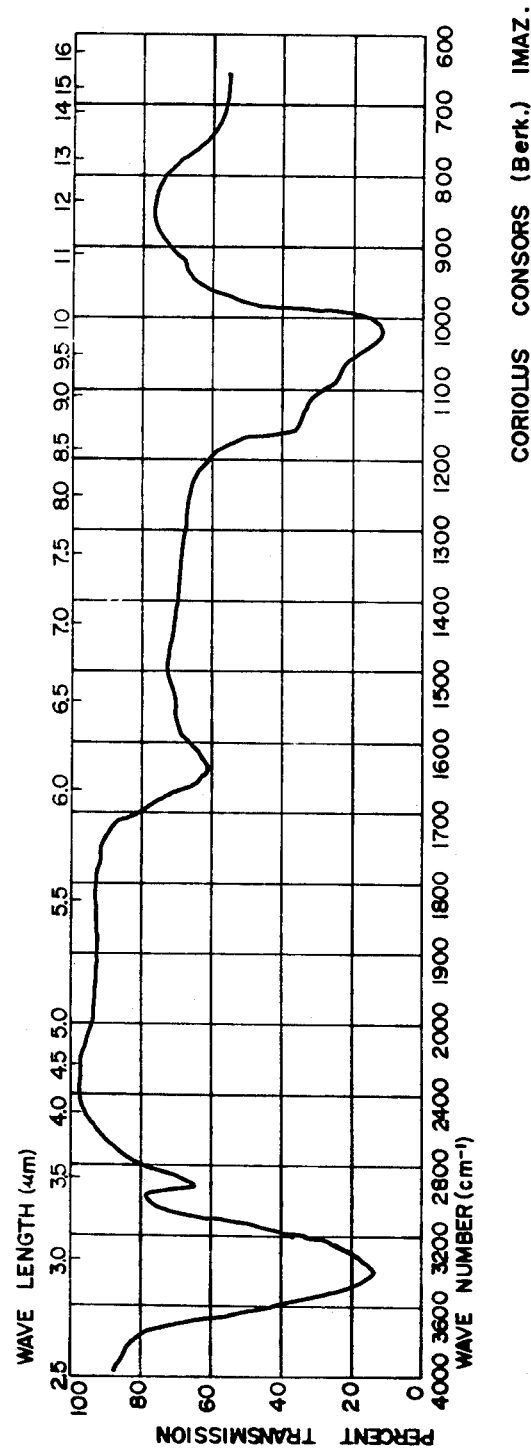
Figure 29:
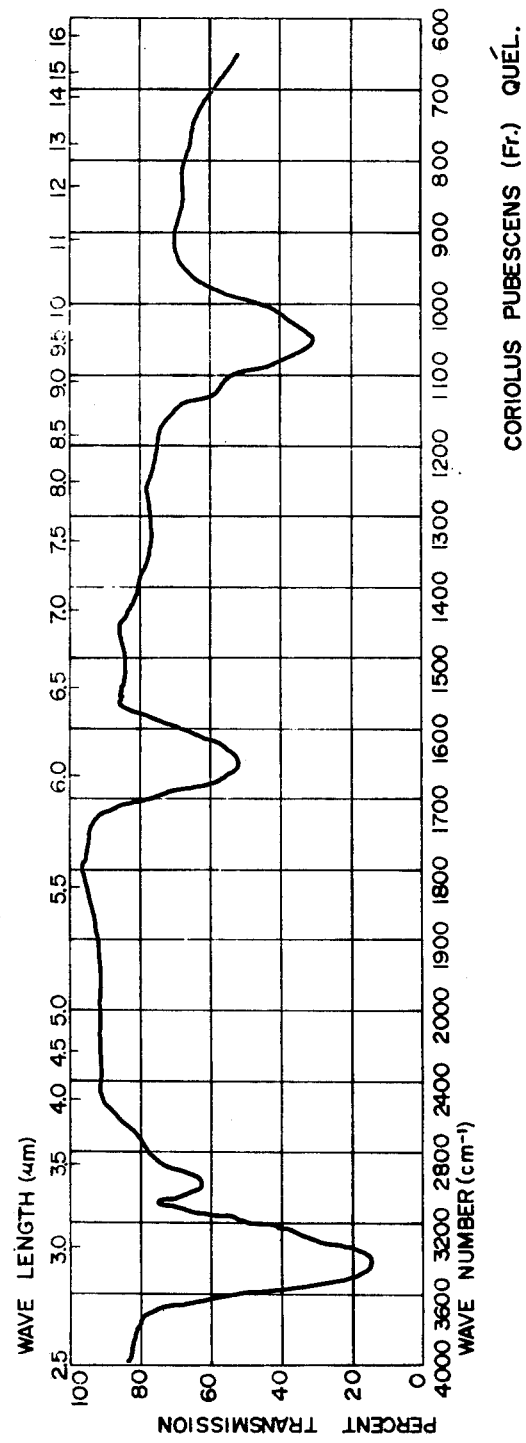

The resulting standard correlation curve which is shown in FIG. 22 shows about 0.5 (Kav) for all of the claimed polysaccharides, leading to the estimate that the molecular weight range of the claimed polysaccharide is within the range $(1.0 – 1.9) \times 10^5$.

The polysaccharides described above exhibit no antimicrobial action to bacteria, fungi and yeasts such as Staphylococus aureus, Escherichia coli, Bacillus subtilis, Aspergillus niger, Candida albicans, etc. and therefore they are quite different from antibacterial anticancer agents such as those obtained from species belonging to Actinomycetes.

In addition, the effective substance exhibits neither cytotoxicity nor the side effects commonly seen in connection with the use of conventional anticancer agents, such as decrease in the number of leucocyte, anemia of liver and other organs, atrophy of spleen, loss of body-weight and loss of appetite. The acute toxicity ($LD_{50}$) of the substance in mice is more than 20 g./kg. for oral administration and more than 100 mg./kg. when subcutaneously injected as an intramuscular or intravenous injection.

The anticarcinogenic activity of each of the polysaccharides of this invention was confirmed according to the following test:

A mouse of ICR-JCL strain weighing 20 g. was inoculated intraperitoneally with solid types of Ehrlich carcinoma or Sarcoma-180 cancer cells. After one week, when a sufficient increase of ascitic fluid was observed in the mouse, the cancer cells therein were subcutaneously transplanted at the axillary area of the other mice at a rate of 6,000,000 cells to each mouse. These selected mice were divided into several groups each composing of ten individuals, the first group (control group) being administered only with saline, and each of the other groups being administered respectively with the polysaccharides of this invention. The first administration of the saline or polysaccharide was made intraperitoneally after one week of the transplantation, the administration thereafter being repeated 9 times every other day. An observation was made of the solid cancer transplanted on the mice, and after 5 days from the last administration (10th) the average increase of body weight was determined and then the mice were anatomized to check side effects and to determine the weight of the tumors removed from the control group as well as those removed from the polysaccharide treated group. The "rate of control" indicated in the following tables was calculated according to the formula:

$$\text{Rate of control (\%)} = (\overline{C} - \overline{T}/\overline{C}) \times 100$$

wherein $\overline{C}$ represents an average weight of the tumors removed from each of the control group mice and $\overline{T}$ represents an average weight of the tumors removed from the polysaccharide treated mice.

The results of this test in relation to each of the claimed "polysaccharides" is set forth in Tables 1 and 2 below.

The following examples will further illustrate the invention:

EXAMPLE 1

Mycelia of Phellnus igniarius (Fr.) Quel. were obtained by incubation in the following culture medium:

| | |
|---|---|
| Peptone | 5 g. |
| Yeast extracts | 3 g. |
| Potassium phosphate (primary) | 0.3 g. |
| Potassium phosphate (secondary) | 0.3 g. |
| Magnesium sulfate (heptahydrate) | 0.3 g. |
| Glucose | 30 g. |
| Water | 1 liter |
| | pH = 6.0 |

The incubation was effected by adding 150 ml. of the above composition to each of one thousand Erlenmary 1 liter flasks. The flasks were stoppered with cotton, sterilized for 30 minutes at 120° C., and inoculated in a conventional manner with a strain of *Phellinus igniarius* (Fr.) Quel. which had been cultured separately in a slant culture medium. After a 20 days stational incubation period at 23° – 25° C., the content of the flask was filtered. The mycelium on the filter was washed with 50 liters of water and then dried and pulverized to fine particles.

2 kg. of this dried and pulverized mycelium of *Phellinus igniarius* (Fr.) Quel. was mixed with 30 liters of distilled water and the mixture heated at 95° – 100° C for 3 hours under agitation in a glass vessel equipped with a reflux condenser to effect extraction. The mixture was allowed to cool to room temperature and then filtered through a filter cloth followed by concentration of the filtrate to one liter. 700 grams of ammonium sulfate were added to the filtrate and the mixture was allowed to stand overnight in an ice-cooled chamber resulting in the formation of a precipitate. Following filtration, the precipitate was washed six times with a saturated ammonium sulfate solution, each washing comprising 4 liters of the solution, i.e., 24 liters in all. The precipitate was then dissolved in water to make about one liter and the aqueous solution was charged into a Visking cellulose tube and subjected to dialysis in flowing water for 40 hours. After concentration of the liquid in the membrane to one liter, 100 ml. of 10% trichloroacetic acid were added to the liquid to remove the free protein and the mixture was decolored with 10 g. of active carbon and then filtered. The filtrate was subjected to further dialysis in flowing water for 40 hours and the liquid in the membrane was concentrated to 100 ml. A precipitate formed by addition of 400 ml. of ethanol was washed in turn with 90% ethanol, 99% ethanol and acetone and dried to yield 29 g. of a grayish white powdery substance.

The substance obtained in the above mentioned procedure is a polysaccharide as is verified by the several tests described above. This substance was analyzed, and was found to have the carbon, hydrogen, nitrogen and oxygen content listed in Table 3 below. But the oxygen content means $[100 - (C + H + N)]\%$ and refer to hereinafter. This compound was also tested for their anticancerous activity, the results being shown in Table 1 below.

EXAMPLE 2

3 kg. of dried and pulverized mycelium of *Gloeoporus amorphus* (Fr.) Clem et Shear (incubated according to the procedure described in Example 1) were mixed with 45 liters of distilled water and the mixture heated in a glass-lined vessel equipped with a reflux concenser at 90° C. for 5 hours under agitation to effect extraction. The mixture was allowed to cool to room temperature and then filtered through a filter cloth followed by concentration of the filtrate to 5 liters. The concentrated liquid was centrifuged for 30 minutes at 1500 G and the resulting supernatant solution admixed under agitation with 4250 g. of ammonium sulfate. The mixture was allowed to stand overnight in an ice chamber resulting in the formation of a precipitate which was filtered. The precipitate was collected, dissolved in water and the solution passed first through a column of Amberlite IR-120B activated with 1-N hydrochloric acid and then through a column of Duolite A-7 activated with 1-N caustic soda, thereby removing the ammonium sulfate. The effluent was concentrated to one liter, homogenized by the addition of 4 liters of ethanol and filtered. The resulting precipitate was first washed with ethanol, then with acetone, and dried to yield 65 g. of a grayish white powdery substance.

The substance obtained in the above-mentioned procedure is a polysaccharide as is verified by the several tests described above. This substance and other polysaccharides obtained from those of other species belonging to Basidiomycetes according to the above-mentioned procedure were analyzed, and were found tohave the carbon hydrogen, nitrogen and oxygen content listed in Table 3 below. These compounds were also tested for their anticancerous activity, the results being shown in Table 1 below.

The other species belonging to Basidiomycetes which were utilized in the above procedure to produce polysaccharides include the following:

MUCRONOPORACEAE

*Hymenochaete mougeotii* (Fr.) Cke.
*Phellinus robustus* (Karst.) Bourd. et Galz.

EXAMPLE 3

1 kg. of dried and pulverized mycelium of Rigidoporus durus (Jungh.) Imaz. (incubated according to the procedure described in Example 1) were mixed with 16 liters of distilled water and the mixture heated in an enameled tank, under agitation at 98° – 100° C. for 3.5 hours to effect extraction. The mixture was allowed to cool to room temperature and then filtered through a filter cloth followed by the concentration of filtrate under reduced pressure to 1.5 liters. Glacial acetic acid was added to be concentrated liquid in an amount sufficient to establish a normality of 1 and the liquid was well stirred. It was then allowed to stand for 24 hours in an ice chamber and centrifuged at 10,000 G for 25 minutes. The supernatant liquid was charged into a cellophane tube and dialyzed for 48 hours in flowing water. The resulting liquid in the membrane was concentrated under reduced pressure to 1.5 liters, admixed with 1275 g. of ammonium sulfate, vigorously stirred, allowed to stand overnight in a cool place and centrifuged at 1250 G for 20 minutes. The resulting precipitate was dissolved in 2 liters of distilled water and subjected to ultrafiltration with Diaflo membrane UM-2 (Amicon Corporation, U.S.A.) at 5 kg./cm$^2$ for 120 hours, with the addition of 60 liters of distilled water. The residual liquid was freeze-dried to obtain 12 g. of a grayish white powdery substance, polysaccharide.

The substance obtained in the above-mentioned procedure is a polysaccharide as is verified by the several tests described above. This substance and other polysaccharides obtained from those of other species belonging to Basidiomycetes according to the above-mentioned procedure were analyzed, and were found to have the carbon, nitrogen, hydrogen and oxygen content listed in Table 3 below. These compounds were also tested for their anticancerous activity, the results being shown in Table 1 below.

The othe species belonging to Basidiomycetes which were utilized in the above procedure to produce polysaccharides include the following:

POLYPORACEAE

*Coltricia pussila* Imazeki et Ysk. Kobayashi
*Rigidoporus ulmarius* (Fr.) Imaz.

MUCRONOPORACEAE

*Inonotus sciurinus* Imazeki

EXAMPLE 4

1 kg. of dried and pulverized mycelium of *Microporus flabelliformis* (Fr.) Kuntze (incubated according to the procedure described in Example 1) were mixed with 35 liters of distilled water and heated with stirring in a stainless steel container, provided with a reflux condenser, at 95° - 98° C. for 5 hours to effect extraction. The mixture was allowed to cool to room temperature and filtered through a filter cloth. The resulting residue was heated together with another 30 liters of distilled water at 98° - 100° C. for 3 hours under agitation to effect further extraction and the mixture, after cooled to room temperature, was again filtered through a filter cloth. Both of the above filtrates were combined and concentrated under reduced pressure to 5 liters. 4 kilograms of ammonium sulfate were added and the mixture was well stirred, allowed to stand overnight at 5° - 8° C. and centrifuged at 1300 G for 20 minutes. The precipitate was dissolved in one liter of distilled water and subjected to ultrafiltration with an ultrafilter Model 2000 (Amicon Corporation) using Diaflo membrane UM-2 (Amicon Corp.) under the condition of 5°-10° C., 5 kg./cm$^2$ and 200 hours. The liquid in the membrane was charged into an Elrenmayer flask and 3% by weight, based on the total mixture, tannic acid was added thereto. The mixture was stirred for 30 minutes and then centrifuged at 300 G for 20 minutes. The resulting supernatant liquid was again subjected to ultrafiltration with said ultrafilter Model 2000 using Diaflo membrane and operating conditions of 5° - 8° C., 5 kg./cm$^2$ and 200 hours. Ethanol was then added to the liquid in the membrane in an amount three times that of liquid. The mixture was well stirred and the precipitate formed was separated by filtration with a filter paper. The precipitate on the filter paper was washed with 5 liters of 75% ethanol, then with 3 liters of 95% ethanol and finally with 1 liter of 99% ethanol. Thereafter, the precipitate was again washed with 1 liter of acetone and dried under reduced pressure to yield 23 g. of a grayish white powdery substance.

The substace obtained in the above-mentiond procedure is a polysaccharide as is verified by the several tests described above. This substance and other polysaccharides obtained from those of other species belonging to Basidiomcetes according to the above-mentioned procedure were analyzed, and were found to have the carbon, hydrogen, nitrogen and oxygen content listed in Table 3 below. These compound were also tested for their anticancerous activity, the results being shown in Table 1 below.

The other species belonging to Basidiomycetes which were utilized in the above procedure to produce polysaccharides include the following:

POLYPORACEAE

*Polyporus pes-caprae* Fr.
*Fomes fomentarious* (Fr.) Kickx
*Coltricia perennis* (Fr.) Murr.
*Favolus alveolarius* (Fr.) Quel.

MUCRONOPORACEAE

*Inonotus kanehirae* (Yasuda) Imazeki, comb, nov.

EXAMPLE 5

2.5 kg. of dried and pulverized mycelium of *Cryptoderma yamanoi Imazeki* (incubated according to the procedure described in Example 1) were mixed with 75 liters of distilled water and heated in a glass vessel, under agitiation, at 95°-100° C. for 3 hours with the occasional addition of an adequate amount of distilled water to effect concentration and extraction to a total volumetric amount of 25 liters. The mixture was allowed to cool to room temperature and was filtered first with a filter cloth and then with filter paper, the filtrate being concentrated under reduced pressure to 2.5 liters. 2 kilograms of ammonium sulfate were added to the liquid and the mixture was vigorously stirred, allowed to stand overnight and filtered through filter paper. The residue on the filter paper was washed with a saturated solution of ammonium sulfate (10 liters) and dissolved in 2.5 liters of distilled water. The solution was then first passed through a column of Duolite C-25-D and then through a column of Amberlite IRA-400 to removed ammonium sulfate. The resulting effluent was concentrated under reduced pressure to 500 ml. and passed through a column of Sephadex G-75. 10 liters of washing water were additionally poured into the column and a fraction containing a substance having the maximum molecular weight was collected and subjected to freeze-drying whereupon 18 g. of a grayish white powdery substance were obtained.

The substance obtained in the above-mentioned procedure is a polysaccharide as is verified by the several tests described above. This substance was analyzed, and was found to have the carbon, hydrogen, nitrogen and oxygen content listed in Table 3 below. This compound was also tested for their anticancerous activity, the results being shown in Table 1 below.

EXAMPLE 6

50 g. of dried and pulverized mycelium of *Piptoprous betulinus* (Fr.) Karst. (obtained according to the procedure of Example 1) were mixed with 2 liters of distilled water and heated with stirring in a glass vessel at 60° C. for 1 hour, and at 95° C. for 3 hours, to effect extraction. The mixture was then allowed to cool to room temperature and filtered through filter paper. 1.5 liters of distilled water were added to the residue and the mixture was stirred at 95° C. for 3 hours to effect further extraction. It was then allowed to cool to room temperature and filtered through a Buchner funnel. These resulting filtrates were combined, concentrated under reduced pressure to 150 ml., and subjected to dialysis in a Visking cellulose tube operated in flowing water for 48 hours.

The dialyzed liquid in the membrane was concentrated under reduced pressure to 100 ml. and centrifuged at 4000 G for 15 minutes to remove insoluble matters. Ethanol was added to the supernatant liquid in a volume four times that of the liquid and the entire mixture was stirred.

The resulting precipitate was centrifuged out at 1500 G for 15 minutes, washed successively with 75% ethanol, 95% ethanol, 99% ethanol and acetone and then dried under reduced pressure for 5 hours at 40° C. to yield 3 g. of a grayish powdery substance. This amounted to 6% of the weight of the starting mycelium and proved to be a crude polysaccharide.

The above procedure was repeated three times in order to obtain 9 g. of the grayish powdery substance which were mixed with 81 ml. of distilled water and the mixture was stirred. To this mixture was added, under agitation, a saturated solution of barium hydroxide so as to adjust the final normality of the liquid to 0.1. A small amount of precipitate formed which was removed by centrifugal separation operated at 1500 G for 20 minutes. To the supernatant liquid was further added, under agitation, a saturated solution of barium hydroxide so as to adjust the final normality of the liquid to 0.3 and thereafter the liquid was centrifuged at 3000 G for 15 minutes. The supernatant liquid was discarded and 100 ml. of 0.3 - N barium hydroxide solution were added to the precipitate. After a thorough agitation, the mixture was further centrifuged at 1500 G for 15 minutes to collect the precipitate. 500 milliliters of distilled water were added to the precipitate and the mixture was thoroughly stripped and similarly subjected to centrifugal separation operated at 1500 G for 15 minutes. This washing with water was repeated 5 times followed by a similar washing with 300 ml. of methanol for each cycle to effect dehydration.

The resulting precipitate was mixed with 70 ml. of 2.4% methanolic solution of hydrogen bromide, the mixture was skaken for 15 minutes and then filtered through filter paper. This procedure was repeated three times using 2.4% methanolic solution of hydrogen bromide followed by a similar treatment, repeated 5 times, using straight methanol instead of the methanolic solution to removed the hydrogen bromide.

When 150 ml. of water were added to the precipitate obtained according to the above mentioned process and the mixture was stirred, the liquid became strongly acidic. Neutralization with 0.3 - N caustic soda resulted in the formation of a gel. The gel was heated as it was at 60° - 70° C. for 30 minutes and then centrifuged at 1500 G for 15 minutes. 200 ml. of water were added to the resulting precipitate, the mixture was thoroughly agitated, and centrifuged under the same conditions. To the resultant gel were added 250 ml. of 0.1 - N caustic soda and the mixture was heated, under agitation, to 60°-70° C. whereby the majority of the gel was dissolved. Insoluble substances were removed by centrifugal separation operated at 1500 G for 30 minutes, the supernatant liquid was neutralized with acetic acid, and then concentrated under reduced pressure to 80 ml. 320 milliliters of ethanol were added to the concentrated liquid resulting in the formation of a precipitate which was washed successively with 75% ethanol, 95% ethanol, 99% ethanol and acetone. The washed precipitate was then dried at 40° C. for 5 hours under reduced pressure to yield 2.73 g. of a grayish white powdery substance.

The substance obtained in the above-mentioned procedure is a polysaccharide as is verified by the several tests described above. This substance and other polysaccharides obtained from those of other species belonging to Basidiomycetes according to the above-mentioned procedure were analyzed, and were found to have the carbon, hydrogen, nitrogen and oxygen content listed in Table 3 below. These compounds were also tested for their anticancerous activity, the results being shown in Table 1 below.

The other species belonging to Basidiomycetes which were utilized in the above procedure to produced polysaccharides include the following:

POLYPROACEAE

Ganoderma tsugae Murrill
*Daedaleopsis tricolor* (Fr.) Bond, et Sing.
*Fomitopsis rosea* (Fr.) Karst.

TABLE 1

| FAMILY/Species | Extracts Dosage mg/kg | Rate of Control (%) Against Sarcoma 180 Solid Cancer | Method of Preparation (Example) |
|---|---|---|---|
| *POLYPORACEAE* | | | |
| Coltricia pusilla Imazaki et Ysk. Kobayashi | 300 | 60 | 3 |
| Fomes fomentarius (Fr.) Kickx | " | 80 | 4 |
| Polyporus pes-caprae Fr. | " | 90 | 4 |
| Fomitopsis rosea (Fr.) Karst. | " | 70 | 6 |
| Rigidoporus ulmarius (Fr.) Imaz. | " | 70 | 3 |
| Coltricia perennis(Fr.) Murr. | " | 80 | 4 |
| Favolus alveolarius (Fr.) Quel. | " | 80 | 4 |
| Ganoderma tsugae Murrill | " | 70 | 6 |
| Rigidoporus durus (Jungh.) Imaz. | " | 50 | 3 |
| Piptoporus betulinus (Fr.) Karst. | " | 90 | 6 |
| Microporus flabelliformis (Fr.) Kuntze | " | 100 | 4 |
| Gloeoporus amorphus (Fr.) Clem.et Shear | " | 60 | 2 |
| Daedaleopsis tricolor (Fr.) Bond. et Sing. | " | 90 | 6 |
| *MUCRONOPORACEAE* | | | |
| Hymenochaete mougeotii (Fr.) Cke. | " | 80 | 2 |
| Inonotus kanehirae (Yasuda) Imazeki, comb. nov. | " | 80 | 4 |
| Phellinus igniarius (Fr.) Quel. | " | 70 | 1 |
| Inonotus sciurinus Imazeki | " | 50 | 3 |
| Cryptoderma yamanoi Imazeki | " | 70 | 5 |
| Phellinus robustus (Karst.) Bourd.et Galz. | " | 70 | 2 |

EXAMPLE 7

According to the process described in Example 1, *Coltricia pusilla* Imazaki et Usk. Kobayashi was incubated and its broth was filtered through a filter cloth to remove the mycelium. The resulting filtrate (100 liters) was concentrated under reduced pressure to 15 liters, 12.75kg of ammonium sulfate were added thereto and then agitiated to dissolve the salt. The solution was allowed to stand overnight in an ice chamber and then centrifuged at 6000 G for 1 hour. The supernatant liquid was discarded and the precipitate was dissolved in 3 liters of distilled water. 2550 grams of ammonium sulfate were added to the solution and the mixture was allowed to stand overnight in an ice chamber followed by centrifugation separation at 6000 G for 1 hour. This treatment was repeated 5 times and the precipitate was dissolved in 3 liters of distilled water. The solution was filtered through a No. 2 filter paper and the filtrate was charged into a cellophane tube and dialyzed in flowing water for 50 hours. The residual liquid in the tube was concentrated at room temperature under a subatmoshperic pressure to 1 liter and trichloroacetic acid was added thereto in an amount sufficient to make it a 4 weight % solution. This solution was then allowed allowed to stand overnight in an ice chamber and centrifuged at 10,000 G for 1 hour. The supernatant liquid was transferred into a cellophane tube and further dialyzed at 10° C. fo 150 hours. The liquid in the tube was concentrated at room temperature under reduced pressure to 1 liter, 3 liters of ethanol were added, and the mixture was allowed to stand overnight. On the next morning, the resulting precipitate was isolated by centrifugal separation, operated at 1500 G for 15 minutes, washed successively with absolute ethanol, acetone and ether and then dried to yield 18.9 g. of a grayish white powdery substance.

The substance obtained in the above-mentioned procedure is a polysaccharide as is verified by the several tests described above. This substance was analyzed, and was found to have the carbon, hydrogen, nitrogen and oxygen content listed in Table 3 below. This compound was also tested for their anticancerous activity, the results being shown in Table 2 below.

EXAMPLE 8

A broth of *Ganodrma tsugae* Murrill prepared under the same condition as that described in Example 7 was filtered through a filter cloth to remove the mycelium. Every 45 liter poriton of the filtrate was concentrated at room temperature under reduced pressure to 4.5 liters and insoluble matters were then removed by centrifugal separation operated at 1300 G for 20 minutes. 3285 grams of ammonium sulfate were added to the supernatant liquid and the mixture was well stirred, allowed to stand overnight in an ice chamber and then centrifuged at 1500 G for 20 minutes. The precipitate was collected, homogenized with 3 liters of a saturated solution of ammonium sulfate and again centrifuged at 1500 G for 20 minutes. The precipitate was dissolved in 1 liter of distilled water and the solution was passed through a column of Amberlite IR-120B activated with hydrochloric acid, to remove a part of free proteins and a part of the ammonium sulfate. The column was then washed with 5 liters of distilled water and the washed solution was combined with the effluent previously obtained, and concentrated at room temperature under reduced pressure to 1.5 liters. Trichloroacetic acid was added to the concentrated liquid to a weight percent of 3.5 and the solution was then allowed to stand overnight in an ice chamber and followed by centrifugation at 10,000 G for 40 minutes to precipitate proteins. The supernatant liquid was passed through a column of Duolite A-7 activated with 4% caustic soda to remove residual ammonium sulfate and coloring matters. The column was washed with 5 liters of distilled water and the washed solution and the effluent previously obtained were combined and then concentrated at room temperature under a subatmospheric pressure to 1.5 liters. 4.5 liters of ethanol were added to the concentrated liquid and the mixture was allowed to stand overnight followed by centrifugation at 1400 G for 20 minutes to collect the resulting precipitate. This prcipitate was then homogenized with 2 liters of 75% ethanol and again subjected to a centrifugal separation operated at 1400 G for 20 minutes. This treatment was repeated 5 times and finally the precipitate was washed successively with absolute ethanol, acetone and ether and dried to yield 2.5 g. of a grayish white powdery substance.

The substance obtained in the above-mentioned procedure is a polysaccharide as is verified by the several tests described above. This substance was analyzed, and was found to have the carbon, hydrogen nitrogen and oxygen content listed in Table 3 below. This compound was also tested for their anticancerous activity, the results being shown in Table 2 below.

EXAMPLE 9

Under the same conditions as described in Example 7, *Cyclomyces fuscus* Kunze was cultivated and the broth (27 liters) was concentrated at room temperature under a subatmospheric pressure to 3 liters. To the concentrated liquid was added acetic acid in an amount sufficient to make 1-N solution which was then stirred thoroughly, allowed to stand for 15 hours in an ice chamber and centrifuged at 10,000 G for 50 minutes. The supernatant liquid was charged into a cellophane tube and dialyzed in flowing water for 80 hours and then the liquid in the tube was concentrated at room temperature under reduced pressure to 3 liters. 2,550 grams of ammonium sulfate were added to the concentrated liquid and the mixture was well agitated, allowed to stand overnight in an ice chamber and centrifuged at 1300 G for 30 minutes. The collected precipitate was homogenized with 1 liter of a saturated solution of ammonium sulfate and again subjected to centrifugal separation, operated at 1300 G for 30 minutes. This treatment was repeated 3 times and the resulting precipitate was dissolved in 3 liters of distilled water. The solution was filtered through a No. 2 filter paper and the filtrate was passed successively through a column of Amberlite IR-120B and a column of Duolite S-30. The columns were washed with 3 liters of distilled water and the washed solution was combined with the effluent previously obtained and concentrated at room temperature under a subtmospheric pressure to 1 liter. 3 liters of ethanol were added to the concentrated liquid and after allowing the mixture to stand overnight a precipitate which formed was then filtered using a No. 5C filter paper (Toyo Filter Paper Co., Ltd.). The precipitate on the filter paper was washed successively with absolute alcohol, acetone and ether and dried to obtain 6.9 g. of a grayish white powdery substance.

The substance obtained in the above-mentioned procedure is a polysaccharide as is verified by the several tests described above. This substance was analyzed, and was found to have the carbon, hydrogen nitrogen and oxygen content listed in Table 3 below. This compound was also tested for their anticancerous activity, the results being shown in Table 2 below.

EXAMPLE 10

A mycelium of *Hymenchaete mougeotii* (Fr.) Cke was obtained by preliminary incubation at 23° – 25° C. for 14 days according to the stationary method in 300 ml. of a culture medium having the following composition:

| | |
|---|---|
| Peptone | 10 g. |
| Yeast extracts | 2 g. |
| Malt extracts | 2 g. |
| Potassium phosphate (Primary) | 0.1 g. |
| Potassium phosphate (Secondary) | 0.1 g. |
| Magnesium sulfate heptahydrate | 0.1 g. |
| Glucose | 50 g. |
| Calcium carbonate | 1.5 g. |
| Water | 1 liter |
| | pH = 6.5 |

The mycelium was homogenized with 100 ml. of a physiological saline and inoculated into 23 liters of a culture medium in a 36 liter stainless steel fermentor.

The culture medium in the fermentor, which had the following composition, was sterilized at 120° C. for 30 minutes and cooled:

| | |
|---|---|
| Peptone | 10 g. |
| Yeast extracts | 2 g. |
| Malt extracts | 2 g. |
| Potassium phosphate (Primary) | 0.1 g. |
| Potassium phosphate (Secondary) | 0.1 g. |
| Magnesium sulfate heptahydrate | 0.1 g. |
| Glucose | 50 g. |
| Silicone resin | 0.05 g. |
| Calcium carbonate | 1 liter |
| | pH = 6.5 |

The medium was subjected to aerobic incubation with stirring for 10 days at 110 - 120 r.p.m., 23° – 25° C. and an aerotion rate of 0.15 liter/liter/min.

The broth (15 liters) was filtered through a filter cloth and the filtrate was concentrated at room temperature under reduced pressure to 1 liter. To the concentrated liquid were added 850 g. of ammonium sulfate, the mixture was well stirred, allowed to stand overnight in an ice chamber and centrifuged at 1600 G for 20 minutes. The resulting precipitate was dissolved in 1 liter of distilled water and the solution was subjected to ultrafiltration using an ultrafilter Model 2000 with Diaflo membranes UM-2 (Amicon Corporation, U.S.A.) under pressure of 7 kg./cm² for 150 hours. The liquid in the filter was transferred into a 3 liter beaker and trichloroacetic acid added so as to produce a 3% by weight solution. This solution was then thoroughly stirred, allowed to stand overnight in an ice chamber and centrifuged at 10,000 G for 1 hour. The supernatant liquid was passed through a column of Duolite A-7 treated with a 4% caustic soda solution. The column was washed with 3 liters of distilled water and the washed solution was combined with the effluent previously obtained and concentrated under reduced pressure to 1 liter. 3 liters of acetone were added to the concentrated liquid and the resulting precipitate was washed with pure acetone, then with ether and dried to obtain 2.6 g. of a grayish white powdery substance.

The substance obtained in the above-mentioned procedure is a polysaccharide as is verified by the several tests described above. This substance was analyzed, and was found to have the carbon, hydrogen, nitrogen and oxygen content listed in Table 3 below. This compound was also tested for its anticancerous activity, the results being shown in Table 2 below.

EXAMPLE 11

220 incubation bottles (1 liter) were each charged with 200 ml. of a medium comprising the so-called Malt extract broth having the following composition:

| | |
|---|---|
| Malt extracts (Difco) | 50 g. |
| Water | 1 liter |

The bottles were stoppered with cotton, sterilized for 30 minutes at 120° C., cooled by allowing to stand and then inoculated with a mycelium of *Gloeoporus amorphus* (Fr.) Clem. et Shear which had been separately cultivated on a slant culture. A stationary incubation was effected at 25° – 28° C., for 20 days and then the fermented broth was filtered through a filter cloth to remove the mycelium. The filtrate was subsequently subjected to ultrafiltration using Diaflo membrane UM-2 under the condition of 7.0 kg./cm² to concentrate the total volume to 3 liters and then the liquid was discharged and subjected to centrifugal separation operated at 1500 G for 15 minutes to remove a residue. 2550 grams of ammonium sulfate were added to the supernatant liquid and the mixture was allowed to stand overnight and centrifuged at 1500 G for 15 minutes. The resulting precipitate was homogenized with 3 liters of a saturated solution of ammonium sulfate and again subjected to centrifugal separation operated at 1500 G for 15 minutes. This treatment was repeated 5 times and then the liquid was passed through a column of Amberlite IR-200 activated with 1-N hydrochloric acid. The column was washed with 1 liter of distilled water and the washing were combined with the effluent, allowed to stand overnight in an ice chamber and subjected to centrifugal separation operated at 10,000 G for 30 minutes. The resulting precipitate was discarded and the supernatant liquid was passed through a column of activated Dowex-1. The effluent was concentrated at room temperature under a reduced pressure to 1 liter, and 3 liters of ethanol were added thereto to produce a precipitate which was filtered, washed in turn with absolute alcohol, acetone and ether and then dried to yield 14.4 g. of a grayish white powdery substance.

The substance obtained in the above-mentioned procedure is a polysaccharide as is verified by the several tests described above. This substance was analyzed, and was found to have the carbon, hydrogen, nitrogen and oxygen content listed in Table 3 below. This compound was also tested for its anticancerous activity, the results being shown in Table 2 below.

EXAMPLE 12

40 Grams of Indian corn powder and 1 liter of water were boiled at 100° C. for 3 hours with continuously supplying water, cooled by allowing to stand, and filtered. 10 g. of cane sugar were then added to the filtrate. 813 incubation bottles of 1 liter were each charged with 180 ml. of the so-called Corn Extract Broth prepared with the above mixing ratio. The bottles were stoppered with cotton, sterilized for 30 minutes at 120° C., allowed to cool to room temperature and then inoculated with a mycelium of previously prepared *Rigidoporus ulmarius* (Fr.) Imaz. A stationary incubation was effected at 23° – 27° C. for 20 days and then the mycelium was removed from the fermented culture medium. The filtrate was then concentrated at room temperature under subatmospheric pressure to 10 liters. 8.5 kilograms of ammonium sulfate were added to the concentrated liquid and the mixture was well stirred, allowed to stand overnight in an ice chamber and filtered. A precipitate on the filter paper was washed with 5 liters of a saturated solution of ammonium sulfate, dissolved in 2 liters of distilled water and then dialyzed in flowing water for 60 hours, using a cellophane tube. The solution in the tube was concentrated to 1 liter and trichloroacetic acid was added thereto in an amount sufficient to make a 3.5% by weight solution which was then allowed to stand overnight in an ice chamber and centrifuged at 10,000 G for 30 minutes. The precipitate was discarded and the supernatant liquid was subjected to ultrafiltration using Diaflo membrane UM-2 of dia. 150 mm under the condition of 7 kg./cm$^2$. Washing and filtration were carried out with 160 liters of distilled water and concentration to 600 ml. was performed by ultrafiltration. 1.8 liters of ethanol were added and the mixture was allowed to stand overnight in an ice chamber and centrifuged at 1600 G for 20 minutes. The precipitate was dissolved in 3 liters of distilled water and removal of ethanol was effected under a reduced pressure with continuous supply water. Freeze-drying of this liquid yielded 29.1 g of a grayish white powdery substance.

The substance obtained in the above-mentioned procedure is a polysaccharide as is verified by the several tests described above. This substance and other polysaccharides obtained from those of other species belonging to Basidiomycetes according to the above-mentioned procedure were analyzed, and were found to have the carbon, hydrogen, nitrogen and oxygen content listed in Table 3 below. These compounds were also tested for their anticancerous activity, the results being shown in Table 2 below.

The other species belonging to Basidiomycetes which were utilized in the above procedure to produce polysaccharides include the following:

POLYPORACEAE

*Rigidoporus durus* (Jungh.) Imaz.

MUCRONOPORACEAE

*Inonotus sciurinus* Imazeki

EXAMPLE 13

177 incubation bottles of 1 liter were each charged with 150 ml. of the so-called Pefer's medium, having the following composition:

| | |
|---|---|
| Glucose | 50 g. |
| Potassium phosphate (Primary) | 5 g. |
| Ammonium nitrite | 10 g. |
| Magnesium sulfate heptahydrate | 2.5 g. |
| Ferric chloride | trace |
| Water | 1 liter |

The bottles were stoppered with cotton, sterilized at 121° C. for 30 minutes and cooled to room temperature. The medium was inoculated with a mycelium of *Fomes fomentarius* (Fr.) Kickx which had been prepared previously and a stationary incubation was effected at 23° – 25° C. for 22 days. The incubated broth was then filtered through a filter cloth and concentrated at room temperature under a reduced pressure to 1 liter.

Trichloroacetic acid was added under agitation to the concentrated liquid in an amount sufficient to make a 4% by weight solution which was then allowed to stand overnight in an ice chamber and centrifuged at 10,000 G for 30 minutes. The precipitate was discarded and the supernatant liquid was passed through a column of Duolite A-7 activated with 4% caustic soda. The column was washed with 3 liters of distilled water and the washing and the effluent previously obtained were combined and concentrated at room temperature under a reduced pressure to 1 liter. 850 grams of ammonium sulfate were added to the concentrated liquid and the mixture was thoroughly stirred, allowed to stand overnight in an ice chamber and centrifuged at 1600 G for 15 minutes. The precipitate was collected, dissolved in 2 liters of distilled water and the solution was subjected to ultrafiltration using Diaflo membrane UM-2 at 7.0 kg/cm$^2$. Washing was effected using 30 liters of distilled water and concentration by ultrafiltration was continued until the liquid finally became 1 liter. The liquid in the filter was then successively passed through columns of activated Duolite C-25D and Amberlite IRA-400, and the columns were washed with 2 liters of distilled water, the washings being combined with the previously obtained effluent and concentrated at room temperature under a subatmospheric pressure to 1 liter. 3 liters of ethanol were added to the concentrated liquid and the mixture was allowed to stand overnight in an ice chamber. The precipitate formed was filtered using a No. 50 filter paper and the residue was washed with 3 liters of 80% ethanol and dissolved in 1 liter of distilled water. With continuous supply of water to the solution, ethanol was removed under a reduced pressure and the solution was then subjected to freeze-drying to yield 3.7 g. of a grayish white powdery substance.

The substance obtained in the above-mentioned procedure is a polysaccharide as is verified by the several tests described above. This substance and other polysaccharides obtained from those of other species belong to Basidiomycetes according to the above-mentioned procedure were analyzed, and were found to have the carbon, hydrogen, nitrogen and oxygen content listed in Table 3 below. These compounds were also tested for their anticancerous activity, the results being shown in Table 2 below.

The other species belonging to Basidiomycetes which were utilized in the above procedure to produce polysaccharides include the following:

PLYPORACEAE

*Polyporus pes-caprae* Fr.
*Microporus flabelliformis* (Fr.) Kuntze

EXAMPLE 14

1324 incubation bottles of 1 liter were each charged with 200 ml. of a medium having the following composition:

| | |
|---|---|
| Glucose | 40 g. |
| Corn steep liquor | 20 g. |
| Sodium nitrite | 3 g. |
| Potassium phosphate (Primary) | 0.5 g. |
| Calcium carbonate | 3 g. |
| Water | 1 liter |

The bottles were heated at 120° C. for 30 minutes for sterilization and then cooled to room temperature. The medium was inoculated with a mycelium of *Piptoporus betulinus* (Fr.) Karst. which had been prepared previously and a stationary incubation was effected at 20° –

23° C. for 21 days. The incubated broth was filtered to remove the mycelium and the filtrate was concentrated at room temperature under a reduced pressure to 10 liters. 30 liters of ethanol were added to the concentrated solution and the mixture was allowed to stand overnight in an ice chamber and filtered through a filter paper. The residue on the filter paper was washed repeatedly with absolute ethanol and then with pure acetone and ether and dried. The dried solid was dissolved in 1 liter of distilled water and the insoluble matters were filtered off using a No. 5C filter paper. 850 grams of ammonium sulfate were added to the filtrate and the mixture was well stirred, allowed to stand overnight in an ice chamber and centrifuged at 1500 G for minutes. The precipitate was collected homogenized with 1 liter of a saturated solution of ammonium sulfate and further centrifuged at 1500 G for 15 minutes. This treatment was repeated 6 times and the precipitate was dissolved in 1 liter of distilled water and passed through a No. 2 filter paper. The filtrate was successively passed through columns of activated Duolite C-27 and Amberlite IR-401, the columns were washed with 2 liters of distilled water, the washings were combined with the effluent and concentrated at room temperature under a reduced pressure to 830 ml. 2490 mililiters of pure acetone were added to the concentrated liquid and the mixture was allowed to stand overnight in an ice chamber and centrifuged at 1500 G for 15 minutes. The precipitate was collected, washed with 3 liters of 75% acetone, and dissolved in 3 liters of distilled water. While continuously supplying water to the solution, acetone was removed under a reduced pressure and the solution was subjected to freeze-drying to yield 38.2 g. of a grayish white powdery substance.

The substance obtained in the above-mentioned procedure is a polysaccharide as is verified by the several tests described above. This substance and other polysaccharides obtained from those of other species belonging to Basidiomycetes according to the above-mentioned procedure were analyzed, and were found to have the carbon, hydrogen, nitrogen and oxygen content listed in Table 3 below. These compounds were also tested for their anticancerous activity, the results being shown in Table 2 below.

The other species belonging to Basidiomycetes which were utilized in the above procedure to produce polysaccharides include the following:

POLYPORACEAE

*Daedaleopsis tricolor* (Fr.) Bond. et Sing.

EXAMPLE 15

220 incubation bottles of 1 liter were each charged with 220 ml. of a so-called Sabouraud's medium having the following composition:

| | |
|---|---|
| Peptone | 10 g. |
| Glucose | 40 g. |
| Water | 1 liter |

The bottles were stoppered with cotton, heated at 120° C. for 30 minutes to effect sterilization and cooled to room temperature. The medium was inoculated with a mycelium of *Oudemansiella radicata* (Fr.) Sing. which had been prepared previously and a stationary incubation was effected at 24° - 26° C. for 18 days. The incubated broth was filtered through a filter cloth to remove the mycelium and the filtrate was concentrated at room temperature under reduced pressure to 3.3 liters and centrifuged at 1300 G for 10 minutes to remove a precipitate. 2460 grams of ammonium sulfate were added to the supernatant liquid and the mixture was well stirred, allowed to stand overnight in an ice chamber and subjected to centrifugal separation operated at 1500 G for 20 minutes. The resulting precipitate was collected, thoroughly homogenized with 3.3 liters of a saturated solution of ammonium sulfate and then subjected to centrifugal separation operated again at 1500 G for 20 minutes. This treatment was repeated 8 times and the resulting precipitate was dissolved in 3 liters of distilled water. The solution was successively passed through ion exchange columns of Dowex-50W and Amberlite IR-401, the columns were washed with 3 liters of distilled water and the washing and the effluent were combined and subjected to ultrafiltration. After washing with 30 liters of distilled water, the ultrafiltration was continued until the total volume of the liquid became 1.1 liter and then the liquid was passed through a column of Duolite S-30 activated with 4% hydrochloric acid and 4% caustic soda. The column was washed with 3 liters of distilled water and the washings were combined with the effluent and concentrated at room temperature under a reduced pressure to 1.1 liter. 3.3 liters of ethanol were added to the concentrated liquid, allowed to stand overnight in an ice chamber and centrifuged at 1500 G for 15 minutes. The resultant precipitate was dissolved into 3 liters of distilled water and the removal of ethanol under reduced pressure was performed at room temperature while continuously supplying water to the solution. Freeze-drying of the residual liquid resulted in 4.8 g. of grayish white powdery substance.

The substance obtained in the above-mentioned procedure is a polysaccharide as is verified by the several tests described above. This substance was analyzed, and was found to have the carbon, hydrogen, nitrogen and oxygen content listed in Table 3 below. This compound was also tested for its anticancerous activity, the results being shown in Table 2 below.

EXAMPLE 16

100 milliliters of a culture medium having the following composition were charged into a 500 ml. shaking flask:

| | |
|---|---|
| Glucose | 100 g. |
| Peptone | 10 g. |
| Ammonium phosphate (Primary) | 2 g. |
| Magnesium sulfate heptahydrate | 0.5 g. |
| Calcium chloride | 0.1 g. |
| Potassium nitrite | 2 g. |
| Water | 1 liter |

The flask was sterilized for 20 minutes under pressure of 1 kg./cm$^2$G. inoculated with a small amount of a mycelium of *Favolus alveolarius* (Fr.) Quel. and incubated under vibration at 23° - 25° C. for 5 days using a reciprocal shaker (110 os./min.). The incubated broth thus obtained was added to 30 liters of a culture medium in a 50 liter sterilized stainless steel tank, and an aerial incubation under agitation was effected for 7 days at 23° - 25° C., 500 r.p.m., and an aeration rate of 0.3 liter/liter/min. The medium was filtered through a filter cloth and the filtrate was concentrated at room temperature under a reduced pressure to 3 liters. Trichloroacetic acid was added to the concentrated liquid in an amount sufficient to provide a 3.3% by weight solution which was then allowed to stand overnight in an ice chamber and centrifuged at 10,000 G for 30 minutes. A precipitate was discarded and the supernatant liquid was charged into a cellophane tube and subjected to dialysis in flowing water for 50 hours. The liquid in the tube membrane was concentrated at room temperature under a reduced pressure to 1 liter, and then 800 g. of ammonium sulfate were added thereto and the mixture was well stirred, allowed to stand overnight in an ice chamber and centrifuged at 1500 G for 15 minutes. The precipitate was collected, homogenized with 3 liters of a saturated solution of ammonium sulfate and subjected to centrifugal separation operated again at 1500 G for 15 minutes. This treatment was repeated 3 times and the resultant precipitate was dissolved into 3 liters of distilled water. The solution was successively passed through columns of activated Amberlite IR-120B and Duolite A-4 and the columns were washed with 3 liters of distilled water. The effluent and washing were combined, concentrated at room temperature under a reduced pressure to 1 liter and passed through a column of Sephadax G-75 swollen with water. A fraction containing larger molecular weight substances was concentrated under a reduced pressure to 1 liter, 3 liters of methanol were added thereto and the mixture was allowed to stand overnight in an ice chamber followed by centrifugal separation operated at 1500 G for 15 minutes. The resulting precipitate was collected and dissolved into 1 liter of distilled water and the methanol removed under reduced pressure while continuously supplying water to the solution. Freeze-drying of the residual liquid yielded 23.1 g. of a grayish white powdery substance.

The substance obtained in the above-mentioned procedure is a polysaccharide as is verified by the several tests described above. This substance was analyzed, and was found to have the carbon, hydrogen, nitrogen and oxygen content listed in Table 3 below. This compound was also tested for its anticancerous activity, the result being shown in Table 2 below.

EXAMPLE 17

205 incubation bottles of 1 liter were each charged with 180 ml. of the so-called Mayer's medium having the following composition:

| | |
|---|---|
| Cane sugar | 50 g. |
| Ammonium nitrite | 10 g. |
| Potassium phosphate (Primary) | 5 g. |
| Magnesium sulfate heptahydrate | 2.5 g. |
| Calcium phosphate | 2.5 g. |
| Water | 1 liter |

The bottles were sterilized under pressure at 120° C. for 30 minutes and cooled to room temperature. The medium was inoculated with a mycelium of *Piptoporus betulinus* (Fr.) Karst. which had been previously incubated, and a stationary incubation was performed at 25° – 27° C. for 20 days.

The incubated broth was filtered through a filter cloth and concentrated at room temperature under a reduced pressure to 2.5 liters. 2 kg. of ammonium sulfate were then added thereto and the mixture was well stirred, allowed to stand overnight and subjected to centrifugal separation operated at 1500 G for 15 minutes. The precipitate was collected and dissolved in 3 liters of distilled water and the solution was passed through a column of activated Amberlite IR-200. The column was washed 1 liter of distilled water, and the washing and the effluent were combined, allowed to stand overnight in an ice chamber and filtered through a filter paper. The filtrate was passed through a column of Duolite A-6 and, the column was washed with 3 liters of distilled water, the filtrate and the washing were combined, and concentrated at room temperature under a reduced pressure to 1 liter. 20 g. of lead acetate were added under agitation to the concentrated liquid and agitation was continued for one hour. The mixture was allowed to stand overnight in an ice chamber and centrifuged at 3000 G for 30 minutes. The precipitate was collected, homogenized with 1 liter of freshly added distilled water and again subjected to centrifugal separation operated at 3000 G for 30 minutes. This treatment was repeated 5 times and the resulting precipitate was suspended in 1 liter of water. Hydrogen sulfide was blown into the suspension for 30 minutes and the resulting precipitate was suspended in 1 liter of water. Hydrogen sulfide was blown into the suspension for 30 minutes and the resulting precipitate was filtered off. The filtrate was placed in an evaporating dish and evaporated on a sand bath with continuous supply of water. After 10 hours, evaporation was completed to dryness without addition of water. The dried solid was dissolved into 1 liter of distilled water and filtered through a No. 5C filter paper and the filtrate was successively passed through columns of activated Duolite C-25D, Amberlite IRA-410 and Duolite S-30. The columns were washed with 1 liter of distilled water and the washings were combined with the effluent and concentrated at room temperature under a reduced pressure to 1 liter. 3 liters of methanol were added to the concentrated liquid and the mixture was allowed to stand overnight in an ice chamber. The resulting precipitate was collected by centrifugal separation operated at 1500 G for 15 minutes and then dissolved in 1 liter of distilled water. Removal of methanol under a reduced pressure was carried out at room temperature while continuously supplying water to the solution. The residual liquid was subjected to freeze-drying whereupon 9.4 g. of a grayish white powdery substance were obtained.

The substance obtained in the above-mentioned procedure is a polysaccharide as is verified by the several tests described above. This substance was analyzed, and was found to have the carbon, hydrogen, nitrogen and oxygen content listed in Table 3 below. This compound was also tested for its anticancerous activity, the results being shown in Table 2 below.

EXAMPLE 18

96 Erlenmayer flasks of 500 ml. were charged each with 80 ml. of a culture medium having the following composition:

| | |
|---|---|
| Peptone | 1 g. |
| Glucose | 3 g. |
| Malt extracts | 0.5 g. |
| Potassium phosphate (primary) | 0.1 g. |
| Water | 1 liter |

The flasks were sterilized for 15 minutes under pressure of 1 kg./cm²G. and the medium was inoculated in a usual manner with a small amount of a mycelium of *Phellinus robustus* (Karst) Bourd. et Galz which had been grown in a slant culture. Incubation was effected at 26° – 28° C. for 5 days using a rotary shaker having a rotary radius of 3.5 cm and rotating at 250 r.p.m.

The incubated culture medium (5 liters) was subjected to centrifugal separation operated at 10,000 G for 15 minutes and the supernatant liquid was passed through a column of Duolite S-30 activated with 4% caustic soda, then through a column of Amberlite IR-120B activated with 1-N hydrochloric acid and finally through a column of Duolite A-7 activated with 4% caustic soda. The columns were washed with 5 liters of distilled water and the washings and the effluent were combined and concentrated at room temperature under a reduced pressure to 500 ml. 1.5 liters of ethanol were added to the concentrated liquid and the mixture was well stirred. The resulting precipitate was centrifuged at 3,000 C for 15 minutes, the resulting precipitate was homogenized with 1 liter of 75% ethanol and again subjected to centrifugal separation operated at 3,000 G for 15 minutes. This treatment was repeated 5 times and the precipitate finally obtained was dissolved in 3 liters of distilled water. Removal of ethanol was carried out under a reduced pressure while continuously supplying distilled water. The residual liquid was subjected to freeze-drying whereupon 1.2 g. of a grayish white powdery substance were obtained.

The substance obtained in the above-mentioned procedure is a polysaccharide as is verified by the several tests described above. This substance and other polysaccharides obtained from those of other species belonging to Basidiomycetes according to the above-mentioned procedure were analyzed, and were found to have the carbon, hydrogen, nitrogen and oxygen content listed in Table 3 below. These compounds were also tested for their anticancerous activity, the results being shown in Table 2 below.

The other species belonging to Basidiomycetes which were utilized in the above procedure to produce polysaccharides include the following:

POLYPORACEAE

*Coltricia perennis* (Fr.) Murr.
*Favolus alveolarius* (Fr.) Quel.
*Fomitopsis rosea* (Fr.) Karst.

MUCRONOPORACEAE

*Phellinus igniarius* (Fr.) Quel.

EXAMPLE 19

A mycelium of *Cryptoderma yamanoi Imazeki* grown in a slant culture was inoculated in a usual manner into 500 ml. of a malt steep liquor in a 3,000 ml. Erlenmayer flask and a stationary incubation was carried out at 25° C. for 13 days. The broth was homogenized and 3 ml. of the homogenized broth was inoculated into 100 ml. of a sterilized malt steep liquor placed in each of 153 shaking flasks of 500 ml. followed by incubation at 25° C. for 4 days at an amplitude of 7 cm and frequency of 120 cycles/min.

The incubated medium obtained by the above procedure was freed from the mycelium and then passed through a column of Duolite C-30 activated by 4% caustic soda. The column was washed with 10 liters of distilled water, the washing was combined with the effluent, and concentrated under a reduced pressure to 1 liter. Lead acetate was added with agitation to the concentrated liquid so as to make a 10% by weight solution which was then allowed to stand overnight in an ice chamber. Next morning, the resulting precipitate was collected by centrifugal separation operated at 10,000 G for 15 minutes, suspended in 1 liter of distilled water and then again centrifuged at 10,000 G for 15 minutes.

This treatment was repeated 3 times and the resulting precipitate was suspended in 1 liter of distilled water. Hydrogen sulfide was sufficiently introduced into the suspension. After allowing to stand for 2 hours, the suspension was filtered through a No. 2 filter paper on which a thin layer of Darco G 60 active carbon had been deposited. While continuously supplying water, the resulting filtrate was concentrated at 65° C. under a reduced pressure until hydrogen sulfide was no longer detected, and then subjected to freeze-drying whereupon 4.8 g. of grayish white powdery substance were obtained.

The substance obtained in the above-mentioned procedure is a polysaccharide as is verified by the several tests described above. This substance and other polysaccharides obtained from those of other species belonging to Basidiomycetes according to the above-mentioned procedure were analyzed, and were found to have the carbon, hydrogen, nitrogen and oxygen content listed in Table 3 below. These compounds were also tested for their anticancerous activity, the results shown in Table 2 below.

The other species belonging to Basidiomycetes which were utilized in the above procedure to produce polysaccharides include the following:

MUCRONOPORACEAE

*Inonotus kanehirae* (Yasuda) Imazeki, comb. nov.

TABLE II

|  | (Cultured Broth) | | | |
|---|---|---|---|---|
|  |  | Rate of Control(%) | | Method of |
| FAMILY/Species | Dosage mg/kg | Sarcoma 180 Solid Cancer | Ehrlich Solid Cancer | Preparation (Example) |
| *POLYPORACEAE* | | | | |
| *Coltricia pusilla Imazeki et Ysk. Kobayashi* | 300 | 100 | 90 | 7 |
| *Fomes fomentarius (Fr.) Kick* | " | 70 | 70 | 13 |
| *Polyporus pes-caprae Fr.* | " | 80 | 90 | 13 |
| *Fomitopsis rosea (Fr.) Karst.* | " | 80 | 90 | 18 |
| *Rigidoporus ulmarius (Fr.) Imaz.* | " | 70 | 80 | 12 |
| *Coltricia perennis (Fr.) Murr.* | " | 100 | 90 | 18 |
| *Favolus alveolarius (Fr.) Quel.* | " | 70 | 60 | 16, 18 |
| *Ganoderma tsugae Murrill* | " | 60 | 60 | 8 |
| *Rigidoporus durus (Jungh.)* | | | | |

TABLE II-continued

| FAMILY/Species | Dosage mg/kg | Rate of Control(%) Sarcoma 180 Solid Cancer | Rate of Control(%) Ehrlich Solid Cancer | Method of Preparation (Example) |
|---|---|---|---|---|
| (Cultured Broth) | | | | |
| Imaz. | " | 100 | 100 | 12 |
| Piptoporus betulinus (Fr.) Karst. | " | 60 | 60 | 14, 17 |
| Microporus flabelliformis (Fr.) Kuntze | " | 90 | 100 | 13 |
| Gloeoporus amorphus (Fr.) Clem.et Shear | " | 90 | 90 | 11 |
| Daedaleopsis tricolor (Fr.) Bond. et Sing. | " | 90 | 90 | 14 |
| MUCRONOPORACEAE | | | | |
| Cyclomyces fuscus Kunze | 300 | 100 | 100 | 9 |
| Hymenochaete mougeotii (Fr.) Cke. | " | 60 | 60 | 10 |
| Inontus kanehirae (Yasuda) Imazeki, comb. nov. | " | 70 | 80 | 19 |
| Phellinus igniarius (Fr.) Quel. | " | 70 | 80 | 18 |
| Inonotus sciurinus Imazeki | " | 60 | 70 | 12 |
| Cryptoderma yamanoi Imazeki | " | 60 | 60 | 19 |
| Phellinus robustus (Karst.) Bourd. et Galz. | " | 60 | 70 | 18 |
| TRICHOLOMARACEAE | | | | |
| Oudemansiella radicata (Fr.) Sing. | 300 | 100 | 90 | 15 |

TABLE III

| FAMILY/Species | C% | H% | N% | O% | Yield Based on Sugar % | Infra-red Spectra (Figure) |
|---|---|---|---|---|---|---|
| POLYPORACEAE | | | | | | |
| Coltricia pusilla Imazeki et Ysk. Kobayashi | 40.0 | 5.1 | 0.2 | 54.7 | 0.60 | 1 |
| Fomes fomentarius (Fr.) Kickx | 39.8 | 5.7 | 0.1 | 54.4 | 0.42 | 2 |
| Polyporus pes-caprae Fr. | 41.6 | 6.4 | 0.3 | 51.7 | 0.89 | 3 |
| Fomitopsis rosea (Fr.) Karst. | 42.8 | 5.3 | trace | 51.9 | 0.78 | 4 |
| Rigidoporus ulmarius (Fr.) Imaz. | 42.0 | 5.2 | 0.2 | 52.6 | 0.97 | 5 |
| Coltricia perennis (Fr.) Murr. | 39.1 | 5.9 | 0.1 | 54.9 | 0.27 | 6 |
| Favolus alveolarius (Fr.) Quel. | 39.4 | 5.4 | 1.3 | 53.9 | 0.77 | 7 |
| Ganoderma tsugae Murrill | 39.6 | 6.5 | 0.1 | 53.8 | 0.19 | 8 |
| Rigidoporus durus (Jungh.) Imaz. | 42.7 | 6.7 | 0.3 | 50.3 | 0.62 | 9 |
| Piptoporus betulinus (Fr.) Karst | 38.6 | 5.4 | 0.5 | 55.5 | 0.53 | 10 |
| Microporus flabelliformis (Fr.) Kuntze | 42.2 | 5.9 | 0.3 | 51.6 | 0.34 | 11 |
| Gloeoporus amorphus (Fr.) Clem. et Shear | 38.3 | 5.8 | 0.1 | 55.8 | 0.96 | 12 |
| Daedaleopsis tricolor (Fr.) Bond. et Sing. | 40.0 | 6.2 | 0.1 | 53.7 | 0.90 | 13 |
| MUCRONOPORACEAE | | | | | | |
| Cyclomyces fuscus Kunze | 41.5 | 6.8 | 0.1 | 51.6 | 0.85 | 14 |
| Hymenochaete mougeotii (Fr.) Cke. | 42.5 | 6.1 | 0.1 | 51.3 | 0.22 | 15 |
| Inonotus kanchirae (Yasuda) Imazeki, comb. nov. | 40.8 | 5.4 | 0.1 | 53.7 | 0.91 | 16 |
| Phellinus igniarius (Fr.) Quel. | 43.0 | 6.5 | trace | 50.5 | 0.43 | 17 |
| Inonotus sciurinus Imazeki | 40.6 | 5.1 | 0.1 | 54.2 | 0.63 | 18 |
| Cryptoderma yamanoi Imazeki | 40.2 | 6.8 | 0.4 | 52.6 | 0.94 | 19 |
| Phellinus robustus (Karst.) Bourd. et Galz. | 38.7 | 5.7 | 0.6 | 55.0 | 0.69 | 20 |
| TRICHOLOMATACEAE | | | | | | |
| Oudemansiella radicata (Fr.) Sing. | 40.0 | 6.1 | 0.7 | 53.2 | 0.36 | 21 |

As indicated in the drawings of infra-red analysis, the polysaccharides produced from the above species show notable absorption at 1600 to 1700 cm$^{-1}$ as well as a broad absorption at 1300 cm$^{-1}$ and 1450 to 1550 cm$^{-1}$.

In addition to the above, various other species of Basidiomycetes were utilized in forming polysaccharides having anticarcinogenic activity. A description of the production of these polysaccharides may be found in applicants' co-pending application Ser. Nos. 513,957 and 514,312, both filed on Oct. 11, 1974, both now abandoned and entitled "Polysaccharides and Method for Producing Same". These disclosures, as well as that of applicants' aforementioned parent application Ser. No. 80,755, now abandoned are incorporated herein by reference.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

EXAMPLE 20

1 kg. of dried and pulverized mycelium of *Coriolus pargamenus* (Fr.) Pat. (incubated according to the procedure described in Example 1) were mixed with 16 liters of distilled water and the mixture heated in an enameled tank, under agitation, at 98°–100° C. for 3.5 hours to effect extraction. The mixture was allowed to cool to room temperature and then filtered through a filter cloth followed by the concentration of filtrate under reduced pressure to 1.5 liters. Glacial acetic acid was added to the concentrated liquid in an amount sufficient to establish a normality of 1 and the liquid was well stirred. It was then allowed to stand for 24 hours in an ice chamber and centrifuged at 10,000 G for 25 minutes. The supernatant liquid was charged into a cellophane tube and dialyzed for 48 hours in flowing water. The resulting liquid in the membrane was concentrated under reduced pressure to 1.5 liters, admixed with 1275 g. of ammonium sulfate, vigorously stirred, allowed to stand overnight in a cool place and centrifuged at 1250 G for 20 minutes. The resulting precipitate was dissolved in 2 liters of distilled water and subjected to ultrafiltration with Diaflo membrane UM-2 (Amicon Corporation, U.S.A.) at 5 kg./cm$^2$ for 120 hours, with the addition of 60 liters of distilled water. The residual liquid was freeze-dried to obtain 5.5g. of a grayish white powdery substance, polysaccharide.

The substance obtained in the above-mentioned procedure is a polysaccharide as is verified by the several tests described above. This substance obtained according to the above-mentioned procedure was analyzed, and was found to have the carbon, hydrogen, nitrogen and oxygen contents listed in Table IV below. This compound was also tested for its anticancerous activity, the results being shown in Table V below.

EXAMPLE 21

2.5 kgs. of dried and pulverized mycelium of *Fomitopsis pinicola* (Fr.) Karst. (incubated according to the procedure described in Example 1) were mixed with 75 liters of distilled water and heated in a glass vessel, under agitation, at 95° – 100° C. for 3 hours with the occasional addition of an adequate amount of distilled water to effect concentration and extraction to a total volumetric amount of 25 liters. The mixture was allowed to cool to room temperature and was filtered first with a filter cloth and then with filter paper, the filtrate being concentrated under reduced pressure to 2.5 liters. 2 kilograms of ammonium sulfate were added to the liquid and the mixture was vigorously stirred, allowed to stand overnight and filtered through filter paper. The residue on the filter paper was washed with a saturated solution of ammonium sulfate (10 liters) and dissolved in 2.5 liters of distilled water. The solution was then first passed through a column of Duolite C-25-D and then through a column of Amberlite IRA-400 to remove ammonium sulfate. The resulting effluent was concentrated under reduced pressure to 500 ml. and passed through a column of Sephadex G-75. 10 liters of washing water were additionally poured into the column and a fraction containing a substance having the maximum molecular weight was collected and subjected to freeze-drying whereupon 10 g. of a grayish white powdery substance were obtained.

The substance obtained in the above-mentioned procedure is a polysaccharide as is verified by the several tests described above. The polysaccharide obtained from Coriolus conchifer (Schw.) Pat. belonging to Basidiomycetes according to the above-mentioned procedure was analyzed, and was found to have the carbon, hydrogen, nitrogen and oxygen contents listed in Table IV below. This latter compound was also tested for its anticancerous activity, the results being shown in Table V below.

EXAMPLE 22

50 g. of dried and pulverized mycelium of *Coriolus versicolor* (Fr.) Quel. (obtained according to the procedure of Example 1) were mixed with 2 liters of distilled water and heated with stirring in a glass vessel at 60° C. for 1 hour, and at 95° C. for 3 hours, to effect extraction. The mixture was then allowed to cool to room temperature and filtered through filter paper. 1.5 liters of distilled water were added to the residue and the mixture was stirred at 95° C. for 3 hours to effect further extraction. It was then allowed to cool to room temperature and filtered through a Buchner funnel. These resulting filtrates were combined, concentrated under reduced pressure to 150 ml., and subjected to dialysis in a Visking cellulose tube operated in flowing water for 48 hours.

The dialyzed liquid in the membrane was concentrated under reduced pressure to 100 ml. and centrifuged at 4000 G for 15 minutes to remove insoluble matters. Ethanol was added to the supernatant liquid in a volume four times that of the liquid and the entire mixture was stirred.

The resulting precipitate was centrifuged out at 1500 G for 15 minutes, washed successively with 75% ethanol, 95% ethanol, 99% ethanol and acetone and then dried under reduced pressure for 5 hours at 40° C. to yield 3 g. of a grayish powdery substance. This amounted to 6% of the weight of the starting mycelium and proved to be crude polysaccharide.

The above procedure was repeated three times in order to obtain 9 g. of the grayish powdery substance which were mixed with 81 ml. of distilled water and the mixture was stirred. To this mixture was added, under agitation, a saturated solution of barium hydroxide so as to adjust the final normality of the liquid to 0.1. A small amount of precipitate formed which was removed by centrifugal separation operated at 1500 G for 20 minutes. To the supernatant liquid was further added, under agitation, a saturated solution of barium hydroxide so as to adjust the final normality of the liquid to 0.3 and thereafter the liquid was centrifuged at 3000 G for 15 minutes. The supernatant liquid was discarded and 100 ml. of 0.3 - N barium hydroxide solution were added to the precipitate. After a thorough agitation, the mixture was further centrifuged at 1500 G for 15 minutes to collect the precipitate. 500 milliliters of distilled water were added to the precipitate and the mixture was thoroughly stripped and similarly subjected to centrifugal separation operated at 1500 G for 15 minutes. This washing with water was repeated 5 times followed by a similar washing with 300 ml. of methanol for each cycle to effect dehydration.

The resulting precipitate was mixed with 70 ml. of 2.4% methanolic solution of hydrogen bromide, the mixture was shaken for 15 minutes and then filtered through filter paper. This procedure was repeated three times using 2.4% methanolic solution of hydrogen bromide followed by a similar treatment, repeated 5 times, using straight methanol instead of the methanolic solution to remove the hydrogen bromide.

When 150 ml. of water was added to the precipitate obtained according to the above-mentioned process and the mixture was stirred, the liquid became strongly acidic. Neutralization with 0.3 - N caustic soda resulted in the formation of a gel. The gel was heated as it was at 60° - 70° C. for 30 minutes and then centrifuged at 1500 G for 15 minutes. 200 ml. of water was added to the resulting precipitate, the mixture was thoroughly agitated, and centrifuged under the same conditions. To the resultant gel were added 250 ml. of 0.1 - N caustic soda and the mixture was heated, under agitation, to 60° - 70° C. whereby the majority of the gel was dissolved. Insoluble substances were removed by centrifugal separation operated at 1500 G for 30 minutes, the supernatant liquid was neutralized with acetic acid, and then concentrated under reduced pressure to 80 ml. 320 milliliters of ethanol were added to the concentrated liquid resulting in the formation of a precipitate which was washed successively with 75% ethanol, 95% ethanol, 99% ethanol and acetone. The washed precipitate was then dried at 40° C. for 5 hours under reduced pressure to yield 3.03 g. of a grayish white powdery substance.

The substance obtained in the above-mentioned procedure is a muco polysaccharide as is verified by the several tests described above. This substance was analyzed, and was found to have the carbon, hydrogen, nitrogen and oxygen contents listed in Table IV below. This compound was also tested for its anticancerous activity, the results being shown in Table V below.

EXAMPLE 23

A mycelium of *Coriolus versicolor* (Fr.) Quel. was obtained by preliminary incubation at 23° - 25° C. for 14 days according to the stationary method in 300 ml. of a culture medium having the following composition:

| | |
|---|---|
| Peptone | 10 g. |
| Yeast extracts | 2 g. |
| Malt extracts | 2 g. |
| Potassium phosphate (Primary) | 0.1 g. |
| Potassium phosphate (Secondary) | 0.1 g. |
| Magnesium sulfate heptahydrate | 0.1 g. |
| Glucose | 50 g. |
| Calcium carbonate | 1.5 g. |
| Water | 1 liter |
| | pH = 6.5 |

The mycelium was homogenized with 100 ml. of a physiological saline and inoculated into 23 liters of a culture medium in a 36 liter stainless steel fermentor.

The culture medium in the fermentor, which had the following composition, was sterilized at 120° C. for 30 minutes and cooled:

| | |
|---|---|
| Peptone | 10 g. |
| Yeast extracts | 2 g. |
| Malt extracts | 2 g. |
| Potassium phosphate (Primary) | 0.1 g. |
| Potassium phosphate (Secondary) | 0.1 g. |
| Magnesium sulfate heptahydrate | 0.1 g. |
| Glucose | 50 g. |
| Silicone resin | 0.05 g. |
| Calcium carbonate | 1 liter |
| | pH = 6.5 |

The medium was subjected to aerobic incubation with stirring for 10 days at 110 - 120 r.p.m., 23° - 25° C. and an aerotion rate of 0.15 liter/liter/min.

The broth (15 liters) was filtered through a filter cloth and the filtrate was concentrated at room temperature under reduced pressure to 1 liter. To the concentrated liquid were added 850 g. of ammonium sulfate, the mixture was well stirred, allowed to stand overnight in an ice chamber and centrifuged at 1600 G for 20 minutes. The resulting precipitate was dissolved in 1 liter of distilled water and the solution was subjected to ultrafiltration using an ultrafilter Model 2000 with Diaflo membranes UM-2 (Amicon Corporation, U.S.A.) under pressure of 7 kg./cm$^2$ for 150 hours. The liquid in the filter was transferred into a 3 liter beaker and trichloroacetic acid added so as to produce a 3% by weight solution. This solution was then thoroughly stirred, allowed to stand overnight in an ice chamber and centrifuged at 10,000 G for 1 hour. The supernatant liquid was passed through a column of Duolite A-7 treated with a 4% caustic soda solution. The column was washed with 3 liters of distilled water and the washed solution was combined with the effluent previously obtained and concentrated under reduced pressure to 1 liter. 3 liters of acetone were added to the concentrated liquid and the resulting precipitate was washed with pure acetone, then with ether and dried to obtain 7.1 g. of a grayish white powdery substance.

The substance obtained in the above-mentioned procedure is a polysaccharide as is verified by the several tests described above. This substance was analyzed and found to have the carbon, hydrogen, nitrogen and oxygen content listed in Table IV below. It was also tested for anticancerous activity, the results being shown in Table VI below.

EXAMPLE 24

220 incubation bottles of 1 liter were each charged with 220 ml. of a so-called Sabouraud's having the following composition:

| | |
|---|---|
| Peptone | 10 g. |
| Glucose | 40 g. |
| Water | 1 liter |

The bottles were stoppered with cotton, heated at 120° C. for 30 minutes to effect sterilization and cooled to room temperature. The medium was inoculated with a mycelium of *Phaeolus schweinitzii* (Fr.) Pat. which had been prepared previously and a stationary incubation was effected at 24°-26° C. for 18 days. The incubated broth was filtered through a filter cloth to remove the mycelium and the filtrate was concentrated at room temperature under reduced pressure to 3.3 liters and centrifuged at 1300 G for 10 minutes to remove a precipitate. 2460 grams of ammonium sulfate were added to the supernatant liquid and the mixture was well stirred, allowed to stand overnight in an ice chamber and subjected to centrifugal separation operated at 1500 G for 20 minutes. The resulting precipitate was collected, thoroughly homogenized with 3.3 liters of a saturated solution of ammonium sulfate and then subjected to centrifugal separation operated again at 1500 G for 20 minutes. This treatment was repeated 8 times and the resulting precipitate was dissolved in 3 liters of distilled water. The solution was successively passed through ion exchange columns of Dowex-50W and Amberlite IR-401, the columns were washed with 3 liters of distilled water and the washing and the effluent were combined and subjected to ultrafiltration. After washing with 30 liters of distilled water, the ultrafiltration was continued until the total volume of the liquid became 1.1 liter and then the liquid was passed through a column of Duolite S-30 activated with 4% hydrochloric acid and 4% caustic soda. The column was washed with 3 liters of distilled water and the washings were combined with the effluent and concentrated at room temperature under a reduced pressure to 1.1 liter. 3.3 liters of ethanol were added to the concentrated liquid, allowed to stand overnight in an ice chamber and centrifuged at 1500 G for 15 minutes. The resultant precipitate was dissolved into 3 liters of distilled water and the removal of ethanol under reduced pressure was performed at room temperature while continuously supplying water to the solution. Freeze-drying of the residual liquid resulted in 2.3 g. of grayish white powdery substance.

The substance obtained in the above-mentioned procedure is a polysaccharide as is verified by the several tests described above. Th polysaccharide obtained from *Coriolus conchifer* (schw.) Pat. belonging to Basidiomycetes according to the above-mentioned procedure was analyzed, and was found to have the carbon, hydrogen, nitrogen and oxygen contents listed in Table IV below. This compound was also tested for its anticancerous activity, the results being shown in Table VI below.

EXAMPLE 25

205 incubation bottles of 1 liter were each charged with 180 ml. of the so-called Mayer's medium having the following composition:

| | |
|---|---|
| Cane sugar | 50 g. |
| Ammonium nitrite | 10 g. |
| Potassium phosphate (Primary) | 5 g. |
| Magnesium sulfate heptahydrate | 2.5 g. |
| Calcium phosphate | 2.5 g. |
| Water | 1 liter |

The bottles were sterilized under pressure at 120° C. for 30 minutes and cooled to room temperature. The medium was inoculated with a mycelium of *Coriolus pargamenus* (Fr.) Pat. which has been previously incubated, and a stationary incubation was performed at 25°–27° C. for 20 days.

The incubated broth was filted through a filter cloth and concentrated at room temperature under a reduced pressure to 2.5 liters. 2 kg. of ammonium sulfate were then added thereto and the mixture was well stirred, allowed to stand overnight and subjected to centrifugal separation operated at 1500 G for 15 minutes. The precipitate was collected and dissolved in 3 liters of distilled water and the solution was passed through a column of activated Amberlite IR-200. The column was washed with 1 liter of distilled water, and the washing and the effluent were combined, allowed to stand overnight in an ice chamber and filtered through a filter paper. The filtrate was passed through a column of Duolite A-6 and, the column was washed with 3 liters of distilled water, the filtrate and the washing were combined, and concentrated at room temperature under a reduced pressure to 1 liter. 20 g. of lead acetate were added under agitation to the concentrated liquid and agitation was continued for one hour. The mixture was allowed to stand overnight in an ice chamber and centrifuged at 3000 G for 30 minutes. The precipitate was collected, homogenized with 1 liter of freshly added distilled water and again subjected to centrifugal separation operated at 3000 G for 30 minutes. This treatment was repeated for 5 times and the resulting precipitate was suspended in 1 liter of water. Hydrogen sulfide was blown into the suspension for 30 minutes and the resulting precipitate was suspended in 1 liter of water. Hydrogen sulfide was blown into the suspension for 30 minutes and the resulting precipitate was filtered off. The filtrate was placed in an evaporation dish and evaporated on a sand bath with continuous supply of water. After 10 hours, evaporation was completed to dryness without addition of water. The dried solid was dissolved into 1 liter of distilled water and filtered through a No. 5C filter paper and the filtrate was successively passed through columns of activated Duolite C-25D, Amberlite IRA-410 and Duolite S-30. The columns were washed with 1 liter of distilled water and the washings were combined with the effluent and concentrated at room temperature under a reduced pressure to 1 liter. 3 liters of methanol were added to the concentrated liquid and the mixture was allowed to stand overnight in an ice chamber. The resulting precipitate was collected by centrifugal separation operated at 1500 G for 15 minutes and then dissolved in 1 liter of distilled water. Removal of methanol under a reduced pressure was carried out at room temperature while continuously supplying water to the solution. The residual liquid was subjected to freeze-drying whereupon 3.2 g. of a grayish white powdery substance were obtained.

The substance obtained in the above-mentioned procedure is a polysaccharide as is verified by the several tests described above. This substance obtained according to the above-mentioned procedure was analyzed, and was found to have the carbon, hydrogen, nitrogen and oxygen contents listed in Table IV below. This compound was also tested for its anticancerous activity, the results being shown in Table VI below.

The following table is divided between two groups, Group A and Group B. As indicated by the infra-red spectra shown in the drawings, the polysaccharides produced from the species of Group A show notable absorption at 3200 to 3600 cm$^{-1}$ (Kayser), whereas Group B products show similar absorption at 950–1200 cm$^{-1}$. Group A products also show a broad and weak absorption at 1200–1450 cm$^{-1}$, whereas Group B polysaccharides show a broad absorption at 1200–1470 cm$^{-1}$ and 1500 cm$^{-1}$–1550 cm$^{-1}$.

TABLE IV

| FAMILY/Species | C% | H% | N% | O% | Yield Based on Sugar % | Infra-red Spectra (FIG.) |
|---|---|---|---|---|---|---|
| *POLYPORACEAE* | | | | | | |

TABLE IV-continued

| FAMILY/Species | C% | H% | N% | O% | Yield Based on Sugar % | Infra-red Spectra (FIG.) |
|---|---|---|---|---|---|---|
| GROUP A | | | | | | |
| Coriolus versicolor (Fr.) Quel. | 38.2 | 6.0 | 2.0 | 53.8 | 0.59 | 23 |
| GROUP B | | | | | | |
| Coriolus conchifer (Schw.) Pat. | 39.5 | 5.4 | 0.1 | 55.0 | 0.55 | 24 |
| Coriolus pargamenus (Fr.) Pat. | 39.5 | 5.0 | 0.6 | 54.9 | 0.18 | 25 |

TABLE V
(EXTRACTS)

| FAMILY/Species | Dosage mg/kg | Rate of Control (%) Against Sarcoma 180 Solid Cancer | Method of Preparation (Example) |
|---|---|---|---|
| POLYPORACEAE | | | |
| Coriolus versicolor (Fr.) Quel. | 300 | 100 | 22 |
| Coriolus conchifer (Schw.) Pat. | 300 | 70 | 21 |
| Coriolus Pargamenus (Fr.) Pat. | 300 | 90 | 3 |

TABLE VI
(Cultured Broth)

| FAMILY/Species | Dosage mg/kg | Rate of Control (%) Sarcoma 180 Solid Cancer | Rate of Control (%) Ehrlich Solid Cancer | Method of Preparation (Example) |
|---|---|---|---|---|
| POLYPORACEAE | | | | |
| Coriolus versicolor (Fr.) Quel. | 300 | 80 | 90 | 23 |
| Coriolus conchifer (Schw.) Pat. | 300 | 80 | 90 | 25 |
| Coriolus pargamenus (Fr.) Pat. | 300 | 60 | 60 | 17 |

EXAMPLE 26

Mycelia of *Aleurodiscus amorphus* Rabenh were obtained by incubation in the following culture medium:

| | |
|---|---|
| Peptone | 5 g. |
| Yeast extracts | 3 g. |
| Potassium phosphate (primary) | 0.3 g. |
| Potassium phosphate (secondary) | 0.3 g. |
| Magnesium sulfate (heptahydrate) | 0.3 g. |
| Glucose | 30 g. |
| Water | 1 liter |
| | pH = 6.0 |

The incubation was effected by adding 150 ml. of the above composition to each of one thousand Erlenmayer 1 liter flasks. The flasks were stoppered with cottom, sterilized for 30 minutes at 120° C., and inoculated in a conventional manner with a strain of *Aleurodiscus amorphus* Rabenh. which had been cultured separately in a slant culture medium. After a 20 days stational incubation period at 23°–25° C., the content of the flaskwas filtered. The mycelium on the filter was washed with 50 liters of water and then dried and pulverized to fine particles.

2 kg. of this dried and pulverized mycelium of *Aleurodiscus amorphus* Rabenh. was mixed with 30 liters of distilled water and the mixture heated at 95°–100° C for 3 hours. under agitation in a glass vessel equipped with a reflux condenser to effect extraction. The mixture was allowed to cool to room temperature and then filtered through a filter cloth followed by concentration of the filtrate to one liter. 700 grams of ammonium sulfate were added to the filtrate and the mixture was allowed to standovernight in an ice-cooled chamber resulting in the formation of a precipitate. Following filtration the precipitate was washed six times with a saturated ammonium sulfate solution, each washing comprising 4 liters of the solution, i.e. 24 liters in all. The precipitate was then dissolved in water to make about one liter and the aqueous solution was charged into a Visking cellulose tube and subjected to dialysis in flowing water for 40 hours. After concentration of the liquid in the membrane to one liter, 100 ml. of 10% trichloroacetic acid were added to the liquid to removed the free protein and the mixture was decolored with 10 g. of active carbon and then filtered. The filtrate was subjected to further dialysis in flowing water for 40 hours and the liquid in the membrane was concentrated to 100 ml. A precipitate formed by addition of 400 ml. of ethanol was washed in turn with 90% ethanol, 99% ethanol and acetone and dried to yield 60 g. of a grayish white powdery substance.

The substrate obtained in the above-mentioned procedure is a polysaccharide as is verified by the several tests described above. The polysaccharide obtained form *Coriolus pubescens* (Fr.) Quel. belonging to Basidiomycetes according to the above-mentioned procedure was analyzed, and was found to have the carbon, hydrogen, and nitrogen contents listed in Table VII below. The oxygen content was calculated at $[100 - (C + H + N)]\%$. This latter compound was also tested for its anticancerous activity, the results being shown in Table VIII below.

EXAMPLE 27

1 kg. of dried and pulverized mycelium of *Daedaleopsis styracina* (P. Henn. et Shir.) Imakei (incubated according to the procedure described in Example 1) were mixed with 35 liters of distilled water and heated with stirring in a stainless steel container, provided with a reflux condenser, at 95°–98° C. for 5 hours to effect extraction. The mixture was allowed to cool to room temperature and filtered through a filter cloth. The resulting residue was heated together with another 30 liters of distilled water at 98°-100° C. for 3 hours under agitation to effect further extraction and the mixture, after cooled to room temperature, was again filtered through a filter cloth. Both of the above filtrates were combined and concentrated under reduced pressure to 5 liters. 4 kilograms of ammonium sulfate were added and the mixture was well stirred, allowed to stand overnight at 5°-8° C. and centrifuged at 1300 G for 20 minutes. The precipitate was dissolved in one liter of distilled water and subjected to ultrafiltration with an ultrafilter Model 2000 (Amicon Corporation) using Daiflo membrane UM-2 (Amicon Corp.) under the conditions of 5°-10° C., 5 kg./cm$^2$ and 200 hours. The liquid in the membrane was charged into an Elrenmayer flask and 3% by weight, based on the total mixture, tannic acid was added thereto. The mixture was stirred for 30 minutes and then centrifuged at 300 G for 20 minutes. The resulting supernatant liquid was again subjected to ultrafiltration with said ultrafilter Model 2000 using Diaflo membrane and operating conditions 5 - 8° C, 5 kg./cm$^2$ and 200 hours. Ethanol was then added to the liquid in the membrane in an amount three times that of liquid. The mixture was well stirred and the precipitate formed was separated by filtration with a filter paper. The precipitate on the filter paper was washed with 5 liters of 75% ethanol, then with 3 liters of 95% ethanol and finally with 1 liter of 99% ethanol. Thereafter, the precipitate was again washed with 1 liter of acetone and dried under reduced pressure to yield 63 g. of a grayish white powdery substance.

The substance obtained in the above-mentioned procedure is a polysaccharide as is verified by the several tests described above. The polysaccharide obtained from *Coriolus consors* (Berk.) Imaz. belonging to Basidiomycetes according to the above-mentioned procedure was analyzed, and was found to have the carbon, hydrogen, nitrogen and oxygen contents listed in Table VII below. This latter compound was also tested for its anticancerous activity, the results being shown in Table VIII below.

EXAMPLE 28

2.5 kg. of dried and pulverized mycelium of *Coriolus hirsutus* (Fr.) Quel. (incubated according to the procedure described in Example 1) were mixed with 75 liters of distilled water and heated in a glass vessel, under agitation, at 95°-100° C. for 3 hours with the occasional addition of an adequate amount of distilled water to effect concentration and extraction of a total volumetric amount of 25 liters. The mixture was allowed to cool to room temperature and was filtered first with a filter cloth and then with filter paper, the filtrate being concentrated under reduced pressure to 2.5 liters. 2 kilograms of ammonium sulfate were added to the liquid and the mixture was vigorously stirred, allowed to stand overnight and filtered through filter paper. The residue on the filer paper was washed with a saturated solution of ammonium sulfate (10 liters) and dissolved in 2.5 liters of distilled water. The solution was then first passed through a column of Duolite C-25-D and then through a column of Amberlite IRA-400 to remove ammonium sulfate. The resulting effluent was concentrated under reduced pressure to 500 ml. and passed through a column of Sephadex G-75. 10 liters of washing water were additionally poured into the column and a fraction containing a substance having the maximum molecular weight was collected and subjected to freeze-drying whereupon 3.26 g. of a grayish white powdery substance were obtained.

The substance obtained in the above-mentioned procedure is a polysaccharide as is verified by the several tests described above. This substance obtained according to the above-mentioned procedure was analyzed, and was found to have the carbon, hydrogen, nitrogen and oxygen contents listed in Table VII below. This compound was also tested for its anticancerous activity, the results being shown in Table VIII below.

EXAMPLE 29

A broth of *Phellinus setulosus* (lloyd Imaz. prepared under the same condition as that described in Example 7 was filtered through a filter cloth to remove the mycelium. Every 45 liter portion of the filtrate was concentrated at room temperature under reduced pressure to 4.5 liters and insoluble matters were then removed by centrifugal separation operated at 1300 G for 20 minutes. 3285 grams of ammonium sulfate were added to the supernatant liquid and the mixture was well stirred, allowed to stand overnight in an ice chamber and then centrifuged at 1500 G for 20 minutes. The precipitate was collected, homogenized with 3 liters of a saturated solution of ammonium sulfate and again centrifuged at 1500 G for 20 minutes. The precipitate was dissolved in 1 liter of distilled water and the solution was passed through a column of Amberlite IR-120B activated with hydrochloric acid, to remove a part of free proteins and a part of the ammonium sulfate. The column was then washed with 5 liters of distilled water and the washed solution was combined with the effluent previously obtained, and concentrated at room temperature under reduced pressure to 1.5 liters. Trichloroacetic acid was added to the concentrated liquid to a weight percent of 3.5 and the solution was then allowed to stand overnight in an ice chamber and followed by centrifugation at 10,000 G for 40 minutes to precipitate free proteins. The supernatant liquid was passed through a column of Duolite A-7 activated with 4% caustic soda to remove residual ammonium sulfate and coloring matters. The column was washed with 5 liters of distilled water and the washed solution and the effluent previously obtained were combined and then concentrated at room temperature under a subatmospheric pressure to 1.5 liters. 4.5 liters of ethanol were added to the concentrated liquid and the mixture was allowed to stand overnight followed by centrifugation at 1400 G for 20 minutes to collect the resulting precipitate. This precipitate was then homogenized with 2 liters of 75% ethanol and again subjected to a centrifugal separation operated at 1400 G for 20 minutes. This treatment was repeated 5 times and finally the precipitate was washed successively with absolute ethanol, acetone and ether and dried to yield 4.4 g. of a grayish white powdery substance.

The substance obtained in the above-mentioned procedure is a polysaccharide as is verified by the several tests described above. The polysaccharide obtained from *Coriolus consors* (Berk.) Imaz. belonging to Basidiomycetes according to the above-mentioned procedure was analyzed, and was found to have the carbon, hydrogen, nitrogen and oxygen contents listed in Table VII below. This latter compound was also tested for its anitcancerous activity, the results being shown in Table IX below.

EXAMPLE 30

A mycelium of *Trametes gibbosa* Fr. was obtained by preliminary incubation at 23°–25° C. for 14 days according to the stationary method in 300 ml. of a culture medium having the following composition:

| | |
|---|---|
| Peptone | 10 g. |
| Yeast extracts | 2 g. |
| Malt extracts | 2 g. |
| Potassium phosphate (Primary) | 0.1 g. |
| Potassium phosphate (Secondary) | 0.1 g. |
| Magnesium sulfate heptahydrate | 0.1 g. |
| Glucose | 50 g. |
| Calcium carbonate | 1.5 g. |
| Water | 1 liter |
| | pH = 6.5 |

The mycelium was homogenized with 100 ml. of a physiological saline and inoculated into 23 liters of a culture medium in a 36 liter stainless steel fermentor.

The culture medium in the fermentor, which had the following composition, was sterilized at 120° C. for 30 minutes and cooled:

| | |
|---|---|
| Peptone | 10 g. |
| Yeast extracts | 2 g. |
| Malt extracts | 2 g. |
| Potassium phosphate (Primary) | 0.1 g. |
| Potassium phosphate (Secondary) | 0.1 g. |
| Magnesium sulfate heptahydrate | 0.1 g. |
| Glucose | 50 g. |
| Silicone resin | 0.05 g. |
| Calcium carbonate | 1 liter |
| | pH = 6.5 |

The medium was subjected to aerobic incubation with stirring for 10 days at 110–120 r.p.m., 23°–25° C. and an aeration rate of 0.15 liter/liter/min.

The broth (15 liters) was filtered through a filter cloth and the filtrate was concentrated at room temperature under reduced pressure to 1 liter. To the concentrated liquid were added 850 g. of ammonium sulfate, the mixture was well stirred, allowed to stand overnight in an ice chamber and centrifuged at 1600 G for 20 minutes. The resulting precipitate was dissolved in 1 liter of distilled water and the solution was subjected to ultrafiltration using an ultrafilter Model 2000 with Diaflo membranes UM-2 (Amicon Corporation, U.S.A.) under pressure of 7 kg./cm$^2$ for 150 hours. The liquid in the filter ws transferred into a 3 liter beaker and trichloroacetic acid added so as to produce a 3% by weight solution. This solution was then thoroughly stirred, allowed to stand overnight in an ice chamber and centrifuged at 10,000 G for 1 hour. The supernatant liquid was passed through a column of Duolite A-7 treated with a 4% caustic soda solution. The column was washed with 3 liters of distilled water and the washed solution was combined with the effluent previously obtained and concentrated under reduced pressure to 1 liter. 3 liters of acetone were added to the concentrated liquid and the resulting precipitate was washed with pure acetone, then with ether and dried to obtain 3.0 g. of a grayish white powdery substance.

The substance obtained in the above-mentioned procedure is a polysaccharide as is verified by the several tests described above. The polysaccharide obtained from *Coriolus pubescens* (Fr.) Quel. belonging to Basidiomycetes according to the above-mentioned procedure was analyzed, and was found to have the carbon, hydrogen, nitrogen and oxygen contents listed in Tabl VII below. This latter compound was also tested for its anticancerous activity, the results being shown in Table IX below.

EXAMPLE 31

177 incubation bottles of 1 liter were each charged with 150 ml. of the so-called Pefer's medium, having the following composition:

| | |
|---|---|
| Glucose | 50 g. |
| Potassium phosphate (Primary) | 5 g. |
| Ammonium nitrite | 10 g. |
| Magnesium sulfate heptahydrate | 2.5 g. |
| Ferric chloride | trace |
| Water | 1 liter |

The bottles were stoppered with cotton, sterilized at 121° C. for 30 minutes and cooled to room temperature. The medium was inoculated with a mycelium of *Hohenbuchelia serotina* (Fr.) Sing. which had been prepared previously and a stationary incubation was effected at 23°–25° C. for 22 days. The incubated broth was then filtered through a filter cloth and cencentrated at room temperature under a reduced pressure to 1 liter. Trichloroacetic acid was added under agitation to the concentrated liquid in an amount sufficient to make a 4% by weight solution which was then allowed to stand overnight in an ice chamber and centrifuged at 10,000 G for 30 minutes. The precipitate was discarded and the supernatant liquid was passed through a column of Duolite A-7 activated with 4% caustic soda. The column was washed with 3 liters of distilled water and the washing and the effluent previously obtained were combined and concentrated at room temperature under a reduced pressure to 1 liter. 850 grams of ammonium sulfate were added to the concentrated liquid and the mixture was thoroughly stirred, allowed to stand overnight in an ice chamber and centrifuged at 1600 G for 15 minutes. The precipitate was collected, dissolved in 2 liters of distilled water and the solution was subjected to ultrafiltration using Diaflo membrane UM-2 at 7.0 kg./cm$^2$. Washing was effected using 30 liters of distilled water and concentration by ultrafiltration was continued until the liquid finally became 1 liter. The liquid in the filter was then successively passed through columns of activated Duolite C-25D and Amberlite IRA-400, and the columns were washed with 2 liters of distilled water, the washings being combined with the previously obtained effluent and concentrated at room temperature under a subatmospheric pressure to 1 liter. 3 liters of ethanol were added to the concentrated liquid and the mixture was allowed to stand overnight in an ice chamber. The precipitate formed was filtered using a No. 5 C filter paper and the residue was washed with 3 liters of 80% ethanol and dissolved in 1 liter of distilled water. With continuous supply of water to the solution, ethanol was removed under a reduced pressure and the solution was then subjected to freeze-drying to yield 1.3 g. of a grayish white powdery substance.

The substance obtained in the above-mentioned procedure is a polysaccharide as is verified by the several tests described above. The polysaccharide obtained from *Coriolus biformis* (Klotz) Pat. belonging to Basidiomycetes according to the above-mentioned procedure was analyzed, and was found to have the carbon, hydrogen, nitrogen and oxygen contents listed in Table VII below. This latter compound was also tested for its anticancerous activity, the results being shown in Table IX below.

EXAMPLE 32

1324 incubation bottles of 1 liter were each charged with 200 ml. of a medium having the following composition:

| | |
|---|---|
| Glucose | 40 g. |
| Corn steep liquor | 20 g. |
| Sodium nitrite | 3 g. |
| Potassium phosphate (Primary) | 0.5 g. |
| Calcium carbonate | 3 g. |
| Water | 1 liter |

The bottles were heated at 120° C. for 30 minutes for sterilization and then cooled to room temperature. The medium was inoculated with a mycelium of *Coriolus hirsutus* (Fr.) Quel. which had been prepared previously and a stationary incubation was effected at 20°–23° C. for 21 days. The incubated broth was filtered to remove the mycelium and the filtrate was concentrated at room temperature under a reduced pressure to 10 liters. 30 liters of ethanol were added to the concentrated solution and the mixture was allowed to stand overnight in an ice chamber and filtered through a filter paper. The residue on the filter paper was washed repeatedly with absolute ethanol and then with pure acetone and ether and dried. The dried solid was dissolved in 1 liter of distilled water and the insoluble matters were filtered off using a No. 5C filter paper. 850 grams of ammonium sulfate were added to the filtrate and the mixture was well stirred, allowed to stand overnight in an ice chamber and centrifuged at 1500 G for minutes. The precipitate was collected homogenized with 1 liter of a saturated solution of ammonium sulfate and further concentrifuged at 1500 G for 15 minutes. This treatment was repeated 6 times and the precipitate was dissolved in 1 liter of distilled water and passed through a No. 2 filter paper. The filtrate was successively passed through columns of activated Duolite C-27 and Amberlite IR-401, the columns were washed with 2 liters of distilled water, the washings were combined with the effluent and concentrated at room temperature under a reduced pressure to 830 ml. 2490 milliliters of pure acetone were added to the concentrated liquid and the mixture was allowed to stand overnight in an ice chamber and centrifuged at 1500 G for 15 minutes. The precipitate was collected, washed with 3 liters of 75% acetone, and dissolved in 3 liters of distilled water. While continuously supplying water to the solution, acetone was removed under a reduced pressure and the solution was subjected to freeze-drying to yield 2.2 g. of grayish white powdery substance.

The substance obtained in the above-mentioned procedure is a polysaccharide as is verified by the several tests described above. This substance obtained according to the above-mentioned procedure was analyzed, and was found to have the carbon, hydrogen, nitrogen and oxygen contents listed in Table VII below. This compound was also tested for its anticancerous activity, the results being shown in Table IX below.

TABLE VII

| FAMILY/Species | C% | H% | N% | O% | Yield Based on Sugar % | Infra-red Spectra (Figure) |
|---|---|---|---|---|---|---|
| POLYPORACEAE | | | | | | |
| *Coriolus hirsutus* (Fr.) Quel. | 42.5 | 5.7 | 1.3 | 50.0 | 0.17 | 26 |
| *Coriolus biformis* (Klotz.) Pat. | 38.4 | 5.9 | 0.1 | 55.6 | 0.21 | 27 |
| *Coriolus consors* (Berk.) Imaz. | 41.5 | 5.7 | 0.5 | 52.3 | 0.77 | 28 |
| *Coriolus pubescens* (Fr.) Quel. | 40.6 | 5.5 | 0.1 53.8 | | 0.20 | 29 |

TABLE VIII
(Extracts)

| FAMILY/Species | Dosage mg/kg | Rate of Control (%) Against Sarcoma 180 Solid Cancer | Method of Preparation (Example) |
|---|---|---|---|
| POLYPORACEAE | | | |
| *Coriolus hirsutus* (Fr.) Quel. | 300 | 90 | 28 |
| *Coriolus consors* (Berk.) Imaz. | 300 | 60 | 27 |
| *Coriolus pubescens* (Fr.) Quel. | 300 | 80 | 26 |

TABLE IX
(Cultured Broth)

| FAMILY/Species | Dosage mg/kg | Sarcoma 180 Solid Cancer | Ehrlich Solid Cancer | Method of Preparation (Example) |
|---|---|---|---|---|
| POLYPORACEAE | | | | |
| *Coriolus hirsutus* (Fr.) Quel. | 300 | 90 | 80 | 32 |
| *Coriolus biformis* (Klotz.) Pat. | 300 | 70 | 60 | 31 |
| *Coriolus consors* (Berk.) Imaz. | 300 | 80 | 90 | 29 |
| *Coriolus pubescens* (Fr.) Quel. | 300 | 70 | 80 | 30 |

We claim:

1. A process for the production of a polysaccharide comprising forming a culture medium or a liquid extract of mycelium of a species of fungi belonging to the class Basidiomycetes and selected from the group consisting of *Coriolus versicolor, Coriolus conchifer, Coriolus pargamenus, Coriolus hirsutus, Coriolus biformis, Coriolus consors* and *Coriolus pubescens,* separating said polysaccharide from the free proteins, and other impurities contained in said culture medium or liquid extract and purifying said polysaccharide to produce a purified polysaccharide having an acute toxicity (LD50) in mice of more than 20 g/kg for oral administration and more than 100 mg/kg for subcutaneous injection.

2. The process of claim 1 wherein said species is *Coriolus versicolor.*

3. The polysaccharide produced by the process of claim 1.

4. A polysaccharide, which in the form of a hydrolyzate, gives positive ninhydrin, anisaldehyde, molisch, anthrone, tryptophane-sulfonic acid, chromotropic acid-sulfuric acid, carbazole cysteine-sulfonic acid, aniline-hydrochloric acid, resorcinol-hydrochloric acid, tollens and thioglycol-sulfuric acid reactions but negative ferric chloride and fehling reactions, said polysaccharide being produced by the process comprising forming a culture medium or a liquid extract of mycelium of a species of fungi belonging to the class Basidiomycetes and selected from the group consisting of *Cori-*

*olus versicolor, Coriolus conchifer, Coriolus pargamenus, Coriolus hirsutus, Coriolus biformis, Coriolus consors* and *Coriolus pubescens,* and separating the polysaccharide from said culture medium or liquid extract.

5. A polysaccharide having a molecular weight within the range of $1.0\text{-}1.9 \times 100000$, as determined by gel filtration, and which, in the form of a hydrolyzate, gives positive ninhydrin, anisaldehyde, molisch, anthrone, tryptophane-sulfonic acid, chromotropic acid-sulfuric acid, carbazole-cysteine-sulfuric acid, aniline-hydrochloric acid, resorcinol-hydrochloric acid, tollens and thioglycol-sulfuric acid reactions but negative ferric chloride and fehling reactions, said polysaccharide being produced by the process comprising forming a culture medium or a liquid extract of mycelium of a species of fungi belonging to the class Basidiomycetes and selected from the group consisting of *Coriolus versicolor, Coriolus conchifer, Coriolus pargamenus, Coriolus hirsutus, Coriolus biformis, Coriolus consors* and *Coriolus pubescens,* and separating the polysaccharide from said culture medium or liquid extract.

6. The polysaccharide produced by the process comprising forming a culture medium or liquid extract of mycelium of a species of fungi belonging to the class Basidiomycetes and selected from the group consisting of *Coriolus versicolor, Coriolus conchifer, Coriolus pargamenus, Coriolus hirsutus, Coriolus biformis, Coriolus consors* and *Coriolus pubescens,* and separating the polysaccharide from said culture medium or liquid extract.

7. The polysaccharide produced by the process comprising forming a culture medium or liquid extract of mycelium of *Coriolus versicolor*, and separating the polysaccharide from said culture medium or liquid extract.

8. The polysaccharide produced by the process of claim 2.

9. The polysaccharide of claim 8, which in the form of a hydrolyzate, gives positive ninhydrin, anisaldehyde, molisch, anthrone, tryptophane-sulfonic acid, chromotropic acid-sulfuric acid, carbazole cysteine-sulfonic acid, anilinehydrochloric acid, resorcinol-hydrochloric acid, tollens and thioglycol-sulfuric acid reactions but negative ferric chloride and fehline reactions.

* * * * *

UNITED STATES PATENT AND TRADEMARK OFFICE
CERTIFICATE OF CORRECTION

PATENT NO. : 4,051,314
DATED : September 27, 1977
INVENTOR(S) : OHTSUKA ET AL

It is certified that error appears in the above-identified patent and that said Letters Patent are hereby corrected as shown below:

```
Column 1, change "necessary" to --necessarily-- in lines
          22 and 23;
          line 25, change "physicochemical" to
          --physiochemical--;
          line 50, change "infiltration" to --filtration--;
          line 54, change "molecule" to --molecular--.

Column 2, line 24, "But" should read --By--.

Column 3, line 5, change "meium" to --medium--;
          line 16, change "comrpises" to read --comprises--;
          line 21, change "combination" to --combinations--;
          line 38, change "combination" to --combinations--.

Column 4, line 20, "dextrane" should read --dextran--;
          line 19, change "pucked" to --packed--;
          line 25, change "product" to --products--;
          line 51, change "is used" to --used is--.

Column 5, line 22, change "reaction" to --reactions--;
          line 27, change "resorcinolhydrochloric" to
          read --resorcinol-hydrochloric--;
          line 28, change "thioglycolsulfuric" to read
          --thioglycol-sulfuric--.

Column 6, line 23, change "axillary" to read --auxiliary--.

Column 7, line 2, "Erlenmary" should read --Erlenmeyer--;
          line 45, change "and refer" to --is referred--;
          line 46, change "their" to --its--;
          line 55, change "concenser" to --condenser--.
```

UNITED STATES PATENT AND TRADEMARK OFFICE
CERTIFICATE OF CORRECTION

PATENT NO. : 4,051,314
DATED : September 27, 1977
INVENTOR(S) : OHTSUKA ET AL

It is certified that error appears in the above-identified patent and that said Letters Patent are hereby corrected as shown below:

Column 8, line 13, after "carbon" insert a comma (,)
line 12, change "tohave" to -- to have--;
line 35, change "be" to --the--.

Column 9, line 29, change "Elrenmayer" to --Erlenmeyer--;
line 50, change "Basidiomcetes" to --Basidiomycetes--.

Column 10, line 35, change "their" to --its--;
line 39, change "Piptoprous" to --Piptoporus.

Column 11, line 24, change "skaken" to --shaken--;
line 29, change "removed" to --remove--.

Column 12, line 28, change "produced" to --produce--;
line 30, change "POLYPROACEAE" to --POLYPORACEAE--.

Column 13, line 4, change "Usk" to --Ysk--;
lines 22 and 23, change "subatmoshperic" to --subatmospheric--;
line 26, delete "allowed";
line 29, change "fo" to --for--;
line 50, change "poriton" to --portion--.

Column 14, line 15, change "prcipitate" to --precipitate--;
line 36, after "make" insert --a--;
line 58, change "subtmospheric" to --subatmospheric--.

Column 18, line 48, change "PLYPORACEAE" to --POLYPORACEAE--.

UNITED STATES PATENT AND TRADEMARK OFFICE
CERTIFICATE OF CORRECTION

PATENT NO. : 4,051,314
DATED : September 27, 1977
INVENTOR(S) : OHTSUKA ET AL

It is certified that error appears in the above-identified patent and that said Letters Patent are hereby corrected as shown below:

Column 23, line 16, change "3,000 C" to --3,000 G--.

Column 25, line 20 of Table II, change "Inontus" to --Itonotus--.

Column 27, delete the first full paragraph before "Example 20".

Column 30, before line 5, change "0.05g.
          1 liter
          pH = 6.5 "   to read --0.05 g.
     1.5 g.
Water  1 liter
     pH = 6.5--.

line 45, before "having" insert --medium--.

Column 31, line 28, change "Th" to --The--;
line 53, change "filted" to --filtered--.

Column 32, line 55, change "3200to" to --3200 to--.

UNITED STATES PATENT AND TRADEMARK OFFICE
CERTIFICATE OF CORRECTION

PATENT NO. : 4,051,314

DATED : September 27, 1977

INVENTOR(S) : OHTSUKA ET AL

It is certified that error appears in the above-identified patent and that said Letters Patent are hereby corrected as shown below:

Column 33 in Table IV, under the heading "O%" change "55.0 0.55" to read --55.0--;

In Table IV, under the heading "Yield Based on Sugar%" change "24" to read --0.55--;

In Table IV, under the heading "Infrared Spectra (FIG.)" change "23

25"

to read -- 23

24

25--;

Column 33, line 54, change "cottom" to --cotton--;
line 58, change "days" to --dav--;

Column 34, line 30, change "standovernight" to --stand overnight--;
line 40, change "removed" to --remove--;
line 63, change "Imakei" to --Imazeki--.

Column 35, line 22, before "5 - 8° C, insert --of--;
line 31, change "yield63" to --yield 63--;
line 59, change "filer" to --filter--.

UNITED STATES PATENT AND TRADEMARK OFFICE
CERTIFICATE OF CORRECTION

PATENT NO. : 4,051,314
DATED : September 27, 1977
INVENTOR(S) : OHTSUKA ET AL

It is certified that error appears in the above-identified patent and that said Letters Patent are hereby corrected as shown below:

Column 36, line 14, change "(lloyd" to --Lloyd--;
line 35, change "concentratedat" to --concentrated at--.

Column 37, lines 29-30, change
"Silicone Resin          0.05 g.
 Calcium carbonate       1 liter
                         pH = 6.5 "

to read
--Silicone resin         0.05 g.
  Calcium carbonate      1.5 g.
  Water                  1 liter
                         pH = 6.5 --.

Column 37, line 47, change "ws" to --was--;
line 67, change "Tabl" to --Table--.

Column 40, Table VII, under the heading "N%" delete 53.8.

Table VII, under the heading "O%", change "0.20" to read --53.8--.

Table VII, under the heading "Yield Based on Sugar%" change "29" to read --0.20--.

UNITED STATES PATENT AND TRADEMARK OFFICE
CERTIFICATE OF CORRECTION

PATENT NO. : 4,051,314
DATED : September 27, 1977
INVENTOR(S) : OHTSUKA ET AL

It is certified that error appears in the above-identified patent and that said Letters Patent are hereby corrected as shown below:

Column 40, Table VII, under the heading "Infrared Spectra (Figure)" change

"27
 28"

to read --27
         28
         29--.

Column 40, line 39, please add the following paragraph:

--The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.--

...Continued

UNITED STATES PATENT AND TRADEMARK OFFICE
CERTIFICATE OF CORRECTION

PATENT NO. : 4,051,314
DATED : September 27, 1977
INVENTOR(S) : OHTSUKA ET AL

It is certified that error appears in the above-identified patent and that said Letters Patent are hereby corrected as shown below:

Column 42, line 22, change "fehline" to read --fehling--.

*Signed and Sealed this Twenty-ninth Day of August 1978*

[SEAL]

Attest:

RUTH C. MASON
*Attesting Officer*

DONALD W. BANNER
*Commissioner of Patents and Trademarks*